United States Patent
Suttin et al.

(10) Patent No.: US 9,668,834 B2
(45) Date of Patent: Jun. 6, 2017

(54) DENTAL SYSTEM FOR DEVELOPING CUSTOM PROSTHESES THROUGH SCANNING OF CODED MEMBERS

(71) Applicant: Biomet 3i, LLC, Palm Beach Gardens, FL (US)

(72) Inventors: Zachary B. Suttin, Jupiter, FL (US); Ross W. Towse, Fort Wayne, IN (US); Gretchen B. Wilson, West Palm Beach, FL (US); Miguel G. Montero, West Palm Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 162 days.

(21) Appl. No.: 14/561,003

(22) Filed: Dec. 4, 2014

(65) Prior Publication Data

US 2015/0173870 A1    Jun. 25, 2015

Related U.S. Application Data

(60) Provisional application No. 61/991,964, filed on May 12, 2014, provisional application No. 61/918,987, filed on Dec. 20, 2013.

(51) Int. Cl.
*A61C 13/00* (2006.01)
*A61C 8/00* (2006.01)
(Continued)

(52) U.S. Cl.
CPC ............ *A61C 8/008* (2013.01); *A61C 8/0001* (2013.01); *A61C 8/0066* (2013.01);
(Continued)

(58) Field of Classification Search
CPC .................................................. A61C 13/0004
See application file for complete search history.

(56) References Cited

U.S. PATENT DOCUMENTS 3,732,621 A    5/1973    Bostrom
3,906,634 A    9/1975    Aspel
(Continued)

FOREIGN PATENT DOCUMENTS

DE    2114323 A1    10/1971
DE    3531389 A1    3/1987
(Continued)

OTHER PUBLICATIONS

"U.S. Appl. No. 14/561,016, Restriction Requirement mailed Aug. 8, 2016", 10 pgs.
(Continued)

*Primary Examiner* — Eric D. Bertram
(74) *Attorney, Agent, or Firm* — Schwegman, Lundberg & Woessner, P.A.

(57) ABSTRACT

A virtual three-dimensional model for use in developing a patient-specific prosthesis to be coupled to an implant installed in a mouth of a patient includes one or more virtual teeth, virtual gingival tissue, and a floating virtual proxy abutment. The virtual gingival tissue includes a virtual gingival aperture leading to a location for a virtual implant. The floating virtual proxy abutment is positioned relative to the virtual gingival aperture and is virtually detached from the rest of the virtual three-dimensional model. The floating virtual proxy abutment has known characteristics for determining a location and an orientation for the patient-specific prosthesis to be attached to the implant.

20 Claims, 15 Drawing Sheets

(51) Int. Cl.
*A61C 13/08* (2006.01)
*A61C 9/00* (2006.01)
*A61C 13/083* (2006.01)

(52) U.S. Cl.
CPC .......... *A61C 8/0077* (2013.01); *A61C 9/0053* (2013.01); *A61C 13/0004* (2013.01); *A61C 13/0019* (2013.01); *A61C 13/08* (2013.01); *A61C 13/0835* (2013.01); *A61C 2008/0084* (2013.01)

(56) References Cited

U.S. PATENT DOCUMENTS

| | | |
|---|---|---|
| 3,919,772 A | 11/1975 | Lenczycki |
| 3,958,471 A | 5/1976 | Muller |
| 4,011,602 A | 3/1977 | Rybicki |
| 4,056,585 A | 11/1977 | Waltke |
| 4,086,701 A | 5/1978 | Kawahara |
| 4,177,562 A | 12/1979 | Miller |
| 4,294,544 A | 10/1981 | Altschuler |
| 4,306,862 A | 12/1981 | Knox |
| 4,325,373 A | 4/1982 | Slivenko |
| 4,341,312 A | 7/1982 | Scholer |
| 4,364,381 A | 12/1982 | Sher |
| 4,439,152 A | 3/1984 | Small |
| 4,543,953 A | 10/1985 | Slocum |
| 4,547,157 A | 10/1985 | Driskell |
| 4,571,180 A | 2/1986 | Kulick |
| 4,611,288 A | 9/1986 | Duret |
| 4,615,678 A | 10/1986 | Moermann |
| 4,624,673 A | 11/1986 | Meyer |
| 4,663,720 A | 5/1987 | Duret |
| 4,713,004 A | 12/1987 | Linkow |
| 4,756,689 A | 7/1988 | Lundgren |
| 4,758,161 A | 7/1988 | Niznick |
| 4,767,331 A | 8/1988 | Hoe |
| 4,772,204 A | 9/1988 | Soderberg |
| 4,793,808 A | 12/1988 | Kirsch |
| 4,821,200 A | 4/1989 | Öberg |
| 4,842,518 A | 6/1989 | Linkow |
| 4,850,870 A | 7/1989 | Lazzara |
| 4,850,873 A | 7/1989 | Lazzara |
| 4,854,872 A | 8/1989 | Detsch |
| 4,856,994 A | 8/1989 | Lazzara |
| 4,872,839 A | 10/1989 | Brajnovic |
| 4,906,191 A | 3/1990 | Soderberg |
| 4,906,420 A | 3/1990 | Brajnovic |
| 4,931,016 A | 6/1990 | Sillard |
| 4,935,635 A | 6/1990 | O'Harra |
| 4,955,811 A | 9/1990 | Lazzara |
| 4,961,674 A | 10/1990 | Wang |
| 4,964,770 A | 10/1990 | Steinbichler |
| 4,986,753 A | 1/1991 | Sellers |
| 4,988,297 A | 1/1991 | Lazzara |
| 4,988,298 A | 1/1991 | Lazzara |
| 4,998,881 A | 3/1991 | Lauks |
| 5,000,685 A | 3/1991 | Brajnovic |
| 5,006,069 A | 4/1991 | Lazzara |
| 5,015,183 A | 5/1991 | Fenick |
| 5,015,186 A | 5/1991 | Detsch |
| 5,030,096 A | 7/1991 | Hurson |
| 5,035,619 A | 7/1991 | Daftary |
| 5,040,982 A | 8/1991 | Stefan/Dogar |
| 5,040,983 A | 8/1991 | Binon |
| 5,064,375 A | 11/1991 | Jörnéus |
| 5,071,351 A | 12/1991 | Green, Jr. |
| 5,073,111 A | 12/1991 | Daftary |
| 5,087,200 A | 2/1992 | Brajnovic |
| 5,100,323 A | 3/1992 | Friedman |
| 5,104,318 A | 4/1992 | Piche |
| 5,106,300 A | 4/1992 | Voitik |
| 5,122,059 A | 6/1992 | Dürr |
| 5,125,839 A | 6/1992 | Ingber |
| 5,125,841 A | 6/1992 | Carlsson |
| 5,133,660 A | 7/1992 | Fenick |
| 5,135,395 A | 8/1992 | Marlin |
| 5,145,371 A | 9/1992 | Jörnéus |
| 5,145,372 A | 9/1992 | Daftary |
| 5,176,516 A | 1/1993 | Koizumi |
| 5,188,800 A | 2/1993 | Green, Jr. |
| 5,195,892 A | 3/1993 | Gersberg |
| 5,205,745 A | 4/1993 | Kamiya |
| 5,209,659 A | 5/1993 | Friedman |
| 5,209,666 A | 5/1993 | Balfour |
| 5,213,502 A | 5/1993 | Daftary |
| 5,221,204 A | 6/1993 | Kruger |
| 5,237,998 A | 8/1993 | Duret |
| 5,246,370 A | 9/1993 | Coatoam |
| 5,257,184 A | 10/1993 | Mushabac |
| 5,281,140 A | 1/1994 | Niznick |
| 5,286,195 A | 2/1994 | Clostermann |
| 5,286,196 A | 2/1994 | Brajnovic |
| 5,292,252 A | 3/1994 | Nickerson |
| 5,297,963 A | 3/1994 | Dafatry |
| 5,302,125 A | 4/1994 | Kownacki |
| 5,312,254 A | 5/1994 | Rosenlicht |
| 5,312,409 A | 5/1994 | McLaughlin |
| 5,316,476 A | 5/1994 | Krauser |
| 5,320,529 A | 6/1994 | Pompa |
| 5,322,436 A | 6/1994 | Horng |
| 5,328,371 A | 7/1994 | Hund |
| 5,334,024 A | 8/1994 | Niznick |
| 5,336,090 A | 8/1994 | Wilson, Jr. |
| 5,338,196 A | 8/1994 | Beaty |
| 5,338,198 A | 8/1994 | Wu |
| 5,343,391 A | 8/1994 | Mushabac |
| 5,344,457 A | 9/1994 | Pilliar |
| 5,350,297 A | 9/1994 | Cohen |
| 5,359,511 A | 10/1994 | Schroeder |
| 5,362,234 A | 11/1994 | Salazar |
| 5,362,235 A | 11/1994 | Daftary |
| 5,368,483 A | 11/1994 | Sutter |
| 5,370,692 A | 12/1994 | Fink |
| 5,372,502 A | 12/1994 | Massen |
| 5,386,292 A | 1/1995 | Massen |
| 5,401,170 A | 3/1995 | Nonomura |
| 5,413,481 A | 5/1995 | Göppel |
| 5,417,569 A | 5/1995 | Perisse |
| 5,417,570 A | 5/1995 | Zuest |
| 5,419,702 A | 5/1995 | Beaty |
| 5,431,567 A | 7/1995 | Datary |
| 5,437,551 A | 8/1995 | Chalifoux |
| 5,440,393 A | 8/1995 | Wenz |
| 5,452,219 A | 9/1995 | Dehoff |
| 5,458,488 A | 10/1995 | Chalifoux |
| 5,476,382 A | 12/1995 | Datary |
| 5,476,383 A | 12/1995 | Beaty |
| 5,492,471 A | 2/1996 | Singer |
| 5,497,336 A | 3/1996 | Andersson |
| 5,516,288 A | 5/1996 | Sichler |
| 5,527,182 A | 6/1996 | Willoughby |
| 5,533,898 A | 7/1996 | Mena |
| 5,538,426 A | 7/1996 | Harding |
| 5,547,377 A | 8/1996 | Daftary |
| 5,556,278 A | 9/1996 | Meitner |
| 5,564,921 A | 10/1996 | Marlin |
| 5,564,924 A | 10/1996 | Kwan |
| 5,569,578 A | 10/1996 | Mushabac |
| 5,575,656 A | 11/1996 | Hajjar |
| 5,580,244 A | 12/1996 | White |
| 5,580,246 A | 12/1996 | Fried |
| 5,595,703 A | 1/1997 | Swaelens |
| 5,613,832 A | 3/1997 | Su |
| 5,613,852 A | 3/1997 | Bavitz |
| 5,616,899 A | 4/1997 | Recigno |
| 5,630,717 A | 5/1997 | Zuest |
| 5,636,986 A | 6/1997 | Prezeshkian |
| 5,651,675 A | 7/1997 | Singer |
| 5,652,709 A | 7/1997 | Andersson |
| 5,658,147 A | 8/1997 | Phimmasone |
| 5,662,476 A | 9/1997 | Ingber |
| 5,674,069 A | 10/1997 | Osorio |
| 5,674,071 A | 10/1997 | Beaty |
| 5,674,073 A | 10/1997 | Ingber |

(56) References Cited

U.S. PATENT DOCUMENTS

| | | |
|---|---|---|
| 5,681,167 A | 10/1997 | Lazarof |
| 5,685,715 A | 11/1997 | Beaty |
| 5,688,283 A | 11/1997 | Knapp |
| 5,704,936 A | 1/1998 | Mazel |
| 5,718,579 A | 2/1998 | Kennedy |
| 5,725,376 A | 3/1998 | Poirier |
| 5,733,123 A | 3/1998 | Blacklock |
| 5,733,124 A | 3/1998 | Kwan |
| 5,741,215 A | 4/1998 | D'Urso |
| 5,743,916 A | 4/1998 | Greenberg |
| 5,759,036 A | 6/1998 | Hinds |
| 5,762,125 A | 6/1998 | Mastrorio |
| 5,762,500 A | 6/1998 | Lazarof |
| 5,768,134 A | 6/1998 | Swaelens |
| 5,769,636 A | 6/1998 | Di Sario |
| 5,791,902 A | 8/1998 | Lauks |
| 5,800,168 A | 9/1998 | Cascione |
| 5,810,592 A | 9/1998 | Daftary |
| 5,813,858 A | 9/1998 | Singer |
| 5,823,778 A | 10/1998 | Schmitt |
| 5,842,859 A | 12/1998 | Palacci |
| 5,846,079 A | 12/1998 | Knode |
| 5,851,115 A | 12/1998 | Carlsson |
| 5,857,853 A | 1/1999 | Van Nifterick |
| 5,871,358 A | 2/1999 | Ingber |
| 5,873,722 A | 2/1999 | Lazzara |
| 5,876,204 A | 3/1999 | Day |
| 5,885,078 A | 3/1999 | Cagna |
| 5,888,034 A | 3/1999 | Greenberg |
| 5,904,483 A | 5/1999 | Wade |
| 5,915,962 A | 6/1999 | Rosenlicht |
| 5,927,982 A | 7/1999 | Kruger |
| 5,938,443 A | 8/1999 | Lazzara |
| 5,954,769 A | 9/1999 | Rosenlicht |
| 5,964,591 A | 10/1999 | Beaty |
| 5,967,777 A | 10/1999 | Klein |
| 5,984,681 A | 11/1999 | Huang |
| 5,989,025 A | 11/1999 | Conley |
| 5,989,029 A | 11/1999 | Osorio |
| 5,989,258 A | 11/1999 | Hattori |
| 5,997,681 A | 12/1999 | Kinzie |
| 6,000,939 A | 12/1999 | Ray |
| 6,008,905 A | 12/1999 | Breton |
| 6,068,479 A | 5/2000 | Kwan |
| 6,093,023 A | 7/2000 | Sala Meseguer |
| 6,099,311 A | 8/2000 | Wagner |
| 6,099,313 A | 8/2000 | Dorken |
| 6,099,314 A | 8/2000 | Kopelman |
| 6,120,293 A | 9/2000 | Lazzara |
| 6,129,548 A | 10/2000 | Lazzara |
| 6,135,773 A | 10/2000 | Lazzara |
| 6,142,782 A | 11/2000 | Lazarof |
| 6,174,168 B1 | 1/2001 | Dehoff |
| 6,175,413 B1 | 1/2001 | Lucas |
| 6,190,169 B1 | 2/2001 | Bluemli |
| 6,197,410 B1 | 3/2001 | Vallittu |
| 6,200,125 B1 | 3/2001 | Akutagawa |
| 6,206,693 B1 | 3/2001 | Hultgren |
| 6,210,162 B1 | 4/2001 | Chishti |
| 6,217,334 B1 | 4/2001 | Hultgren |
| 6,227,859 B1 | 5/2001 | Sutter |
| 6,257,890 B1 | 7/2001 | Khoury |
| 6,273,720 B1 | 8/2001 | Spalten |
| 6,283,753 B1 | 9/2001 | Willoughby |
| 6,287,119 B1 | 9/2001 | van Nifterick |
| 6,296,483 B1 | 10/2001 | Champleboux |
| 6,305,939 B1 | 10/2001 | Dawood |
| 6,312,260 B1 | 11/2001 | Kumar |
| 6,319,000 B1 | 11/2001 | Branemark |
| 6,322,728 B1 | 11/2001 | Brodkin |
| 6,334,853 B1 | 1/2002 | Kopelman |
| 6,382,975 B1 | 5/2002 | Poirier |
| 6,402,707 B1 | 6/2002 | Ernst |
| 6,406,295 B1 | 6/2002 | Mahler |
| 6,431,867 B1 | 8/2002 | Gittelson |
| 6,488,503 B1 | 12/2002 | Lichkus |
| 6,497,574 B1 | 12/2002 | Miller |
| 6,540,784 B2 | 4/2003 | Barlow |
| 6,558,162 B1 | 5/2003 | Porter |
| 6,568,936 B2 | 5/2003 | MacDougald |
| 6,575,751 B1 | 6/2003 | Lehmann |
| 6,594,539 B1 | 7/2003 | Geng |
| 6,610,079 B1 | 8/2003 | Li |
| 6,619,958 B2 | 9/2003 | Beaty |
| 6,629,840 B2 | 10/2003 | Chishti |
| 6,634,883 B2 | 10/2003 | Ranalli |
| 6,648,640 B2 | 11/2003 | Rubbert |
| 6,671,539 B2 | 12/2003 | Gateno |
| 6,672,870 B2 | 1/2004 | Knapp |
| 6,688,887 B2 | 2/2004 | Morgan |
| 6,691,764 B2 | 2/2004 | Embert |
| 6,743,491 B2 | 6/2004 | Cirincione |
| 6,755,652 B2 | 6/2004 | Nanni |
| 6,772,026 B2 | 8/2004 | Bradbury |
| 6,776,614 B2 | 8/2004 | Wiechmann |
| 6,783,359 B2 | 8/2004 | Kapit |
| 6,790,040 B2 | 9/2004 | Amber |
| 6,793,491 B2 | 9/2004 | Klein |
| 6,808,659 B2 | 10/2004 | Schulman |
| 6,814,575 B2 | 11/2004 | Poirier |
| 6,821,462 B2 | 11/2004 | Schulman |
| 6,829,498 B2 | 12/2004 | Kipke |
| D503,804 S | 4/2005 | Phleps |
| 6,882,894 B2 | 4/2005 | Durbin |
| 6,885,464 B1 | 4/2005 | Pfeiffer |
| 6,902,401 B2 | 6/2005 | Jorneus |
| 6,913,463 B2 | 7/2005 | Blacklock |
| 6,926,442 B2 | 8/2005 | Stöckl |
| 6,926,525 B1 | 8/2005 | Ronvig |
| 6,939,489 B2 | 9/2005 | Moszner |
| 6,942,699 B2 | 9/2005 | Stone |
| 6,953,383 B2 | 10/2005 | Rothenberger |
| 6,957,118 B2 | 10/2005 | Kopelman |
| 6,966,772 B2 | 11/2005 | Malin |
| 6,970,760 B2 | 11/2005 | Wolf |
| 6,971,877 B2 | 12/2005 | Harter |
| 6,994,549 B2 | 2/2006 | Brodkin |
| 7,010,150 B1 | 3/2006 | Pfeiffer |
| 7,010,153 B2 | 3/2006 | Zimmermann |
| 7,012,988 B2 | 3/2006 | Adler |
| 7,018,207 B2 | 3/2006 | Prestipino |
| 7,021,934 B2 | 4/2006 | Aravena |
| 7,029,275 B2 | 4/2006 | Rubbert |
| 7,044,735 B2 | 5/2006 | Malin |
| 7,056,115 B2 | 6/2006 | Phan |
| 7,056,472 B1 | 6/2006 | Behringer |
| 7,059,856 B2 | 6/2006 | Marotta |
| 7,066,736 B2 | 6/2006 | Kumar |
| 7,084,868 B2 | 8/2006 | Farag |
| 7,086,860 B2 | 8/2006 | Schuman |
| 7,097,451 B2 | 8/2006 | Tang |
| 7,104,795 B2 | 9/2006 | Dadi |
| 7,110,844 B2 | 9/2006 | Kopelman |
| 7,112,065 B2 | 9/2006 | Kopelman |
| 7,118,375 B2 | 10/2006 | Durbin |
| D532,991 S | 12/2006 | Gozzi |
| 7,153,132 B2 | 12/2006 | Tedesco |
| 7,153,135 B1 | 12/2006 | Thomas |
| 7,163,443 B2 | 1/2007 | Basler |
| 7,175,434 B2 | 2/2007 | Brajnovic |
| 7,175,435 B2 | 2/2007 | Andersson |
| 7,178,731 B2 | 2/2007 | Basler |
| 7,214,062 B2 | 5/2007 | Morgan |
| 7,220,124 B2 | 5/2007 | Taub |
| 7,228,191 B2 | 6/2007 | Hofmeister |
| 7,236,842 B2 | 6/2007 | Kopelman |
| 7,281,927 B2 | 10/2007 | Marotta |
| 7,286,954 B2 | 10/2007 | Kopelman |
| 7,303,420 B2 | 12/2007 | Huch |
| 7,319,529 B2 | 1/2008 | Babayoff |
| 7,322,746 B2 | 1/2008 | Beckhaus |
| 7,322,824 B2 | 1/2008 | Schmitt |
| 7,324,680 B2 | 1/2008 | Zimmermann |
| 7,329,122 B1 | 2/2008 | Scott |

(56) References Cited

U.S. PATENT DOCUMENTS

| | | |
|---|---|---|
| 7,333,874 B2 | 2/2008 | Taub |
| 7,335,876 B2 | 2/2008 | Eiff |
| D565,184 S | 3/2008 | Royzen |
| 7,367,801 B2 | 5/2008 | Saliger |
| 7,379,584 B2 | 5/2008 | Rubbert |
| D571,471 S | 6/2008 | Stöckl |
| 7,381,191 B2 | 6/2008 | Fallah |
| 7,383,094 B2 | 6/2008 | Kopelman |
| D575,747 S | 8/2008 | Abramovich |
| 7,421,608 B2 | 9/2008 | Schron |
| 7,425,131 B2 | 9/2008 | Amber |
| 7,429,175 B2 | 9/2008 | Gittelson |
| 7,435,088 B2 | 10/2008 | Brajnovic |
| 7,476,100 B2 | 1/2009 | Kuo |
| 7,481,647 B2 | 1/2009 | Sambu |
| 7,488,174 B2 | 2/2009 | Kopelman |
| 7,497,619 B2 | 3/2009 | Stoeckl |
| 7,497,983 B2 | 3/2009 | Khan |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman |
| 7,545,372 B2 | 6/2009 | Kopelman |
| 7,551,760 B2 | 6/2009 | Scharlack |
| 7,555,403 B2 | 6/2009 | Kopelman |
| 7,556,496 B2 | 7/2009 | Cinader, Jr. |
| 7,559,692 B2 | 7/2009 | Beckhaus |
| 7,563,397 B2 | 7/2009 | Schulman |
| D597,769 S | 8/2009 | Richter |
| 7,572,058 B2 | 8/2009 | Pruss |
| 7,572,125 B2 | 8/2009 | Brajnovic |
| 7,574,025 B2 | 8/2009 | Feldman |
| 7,578,673 B2 | 8/2009 | Wen |
| 7,580,502 B2 | 8/2009 | Dalpiaz |
| 7,581,951 B2 | 9/2009 | Lehmann |
| 7,582,855 B2 | 9/2009 | Pfeiffer |
| 7,628,537 B2 | 12/2009 | Schulze-Ganzlin |
| 7,632,097 B2 | 12/2009 | Clerck |
| 7,653,455 B2 | 1/2010 | Cnader, Jr. |
| 7,654,823 B2 | 2/2010 | Dadi |
| 7,655,586 B1 | 2/2010 | Brodkin |
| 7,658,610 B2 | 2/2010 | Knopp |
| 7,661,956 B2 | 2/2010 | Powell |
| 7,665,989 B2 | 2/2010 | Brajnovic |
| 7,679,723 B2 | 3/2010 | Schwotzer |
| 7,687,754 B2 | 3/2010 | Eiff |
| 7,689,308 B2 | 3/2010 | Holzner |
| D614,210 S | 4/2010 | Basler |
| 7,698,014 B2 | 4/2010 | Dunne |
| 7,774,084 B2 | 8/2010 | Cinader, Jr. |
| 7,780,907 B2 | 8/2010 | Schmidt |
| 7,785,007 B2 | 8/2010 | Stoeckl |
| 7,787,132 B2 | 8/2010 | Körner |
| 7,796,811 B2 | 9/2010 | Orth |
| 7,798,708 B2 | 9/2010 | Erhardt |
| 7,801,632 B2 | 9/2010 | Orth |
| 7,815,371 B2 | 10/2010 | Schulze/Ganzlin |
| 7,824,181 B2 | 11/2010 | Sers |
| D629,908 S | 12/2010 | Jerger |
| 7,855,354 B2 | 12/2010 | Eiff |
| 7,865,261 B2 | 1/2011 | Pfeiffer |
| 7,876,877 B2 | 1/2011 | Stockl |
| 7,901,209 B2 | 3/2011 | Saliger |
| 7,982,731 B2 | 7/2011 | Orth |
| 7,985,119 B2 | 7/2011 | Basler |
| 7,986,415 B2 | 7/2011 | Thiel |
| 7,988,449 B2 | 8/2011 | Amber |
| 8,011,925 B2 | 9/2011 | Powell |
| 8,011,927 B2 | 9/2011 | Berckmans, III |
| 8,026,943 B2 | 9/2011 | Weber |
| 8,038,440 B2 | 10/2011 | Swaelens |
| 8,047,895 B2 | 11/2011 | Basler |
| 8,057,912 B2 | 11/2011 | Basler |
| 8,062,034 B2 | 11/2011 | Hanisch |
| 8,083,522 B2 | 12/2011 | Karkar |
| 8,105,081 B2 | 1/2012 | Bavar |
| 8,185,224 B2 | 5/2012 | Powell |
| 8,353,703 B2 | 1/2013 | Amber |
| 8,777,612 B2 | 7/2014 | Suttin |
| 8,932,058 B2 | 1/2015 | Fisker |
| 8,944,816 B2 | 2/2015 | Robb |
| 2001/0008751 A1 | 7/2001 | Chishti |
| 2001/0034010 A1 | 10/2001 | MacDougald |
| 2002/0010568 A1 | 1/2002 | Rubbert |
| 2002/0028418 A1 | 3/2002 | Farag |
| 2002/0039717 A1 | 4/2002 | Amber |
| 2002/0160337 A1 | 10/2002 | Klein |
| 2002/0167100 A1 | 11/2002 | Moszner |
| 2003/0044753 A1 | 3/2003 | Marotta |
| 2003/0130605 A1 | 7/2003 | Besek |
| 2003/0222366 A1 | 12/2003 | Stangel |
| 2004/0029074 A1 | 2/2004 | Brajnovic |
| 2004/0048227 A1 | 3/2004 | Brajnovic |
| 2004/0137408 A1 | 7/2004 | Embert |
| 2004/0157188 A1 | 8/2004 | Luth |
| 2004/0180308 A1 | 9/2004 | Ebi |
| 2004/0219477 A1 | 11/2004 | Harter |
| 2004/0219479 A1 | 11/2004 | Malin |
| 2004/0219490 A1 | 11/2004 | Gartner |
| 2004/0220691 A1 | 11/2004 | Hofmeister |
| 2004/0241611 A1 | 12/2004 | Amber |
| 2004/0243481 A1 | 12/2004 | Bradbury |
| 2004/0259051 A1 | 12/2004 | Brajnovic |
| 2005/0023710 A1 | 2/2005 | Brodkin |
| 2005/0056350 A1 | 3/2005 | Dolabdjian |
| 2005/0070782 A1 | 3/2005 | Brodkin |
| 2005/0084144 A1 | 4/2005 | Feldman |
| 2005/0100861 A1 | 5/2005 | Choi |
| 2005/0170311 A1 | 8/2005 | Tardieu |
| 2005/0271996 A1 | 12/2005 | Sporbert |
| 2005/0277089 A1 | 12/2005 | Brajnovic |
| 2005/0277090 A1 | 12/2005 | Anderson |
| 2005/0277091 A1 | 12/2005 | Andersson |
| 2005/0282106 A1 | 12/2005 | Sussman |
| 2005/0283065 A1 | 12/2005 | Babayoff |
| 2006/0006561 A1 | 1/2006 | Brajnovic |
| 2006/0008763 A1 | 1/2006 | Brajnovic |
| 2006/0008770 A1 | 1/2006 | Brajnovic |
| 2006/0093988 A1 | 5/2006 | Swaelens |
| 2006/0094951 A1 | 5/2006 | Dean |
| 2006/0099545 A1 | 5/2006 | Lai |
| 2006/0127848 A1 | 6/2006 | Sogo |
| 2006/0210949 A1 | 9/2006 | Stoop |
| 2006/0263741 A1 | 11/2006 | Imgrund |
| 2006/0281041 A1 | 12/2006 | Rubbert |
| 2007/0015111 A1 | 1/2007 | Kopelman |
| 2007/0031790 A1 | 2/2007 | Raby |
| 2007/0065777 A1 | 3/2007 | Becker |
| 2007/0077532 A1 | 4/2007 | Harter |
| 2007/0092854 A1 | 4/2007 | Powell |
| 2007/0141525 A1 | 6/2007 | Cinader, Jr. |
| 2007/0211081 A1 | 9/2007 | Quadling |
| 2007/0218426 A1 | 9/2007 | Quadling |
| 2007/0269769 A1 | 11/2007 | Marchesi |
| 2007/0281277 A1 | 12/2007 | Brajnovic |
| 2008/0038692 A1 | 2/2008 | Andersson |
| 2008/0044794 A1 | 2/2008 | Brajnovic |
| 2008/0057467 A1 | 3/2008 | Gittelson |
| 2008/0070181 A1 | 3/2008 | Abolfathi |
| 2008/0085489 A1 | 4/2008 | Schmitt |
| 2008/0090210 A1 | 4/2008 | Brajnovic |
| 2008/0114371 A1 | 5/2008 | Kluger |
| 2008/0118895 A1 | 5/2008 | Brajnovic |
| 2008/0124676 A1 | 5/2008 | Marotta |
| 2008/0153060 A1 | 6/2008 | De Moyer |
| 2008/0153061 A1 | 6/2008 | Marcello |
| 2008/0153065 A1 | 6/2008 | Brajnovic |
| 2008/0153069 A1 | 6/2008 | Holzner |
| 2008/0176189 A1 | 7/2008 | Stonisch |
| 2008/0206714 A1 | 8/2008 | Schmitt |
| 2008/0233537 A1 | 9/2008 | Amber |
| 2008/0241798 A1 | 10/2008 | Holzner |
| 2008/0261165 A1 | 10/2008 | Steingart |
| 2008/0286722 A1 | 11/2008 | Berckmans, III |

(56) References Cited

U.S. PATENT DOCUMENTS

| | | |
|---|---|---|
| 2008/0300716 A1 | 12/2008 | Kopelman |
| 2009/0017418 A1 | 1/2009 | Gittelson |
| 2009/0026643 A1 | 1/2009 | Wiest |
| 2009/0042167 A1 | 2/2009 | Van Der Zel |
| 2009/0081616 A1 | 3/2009 | Pfeiffer |
| 2009/0087817 A1 | 4/2009 | Jansen |
| 2009/0092948 A1 | 4/2009 | Gantes |
| 2009/0098510 A1 | 4/2009 | Zhang |
| 2009/0098511 A1 | 4/2009 | Zhang |
| 2009/0123045 A1 | 5/2009 | Quadling |
| 2009/0123887 A1 | 5/2009 | Brajnovic |
| 2009/0130630 A1 | 5/2009 | Suttin |
| 2009/0187393 A1 | 7/2009 | Van Lierde |
| 2009/0220134 A1 | 9/2009 | Cahill |
| 2009/0220916 A1 | 9/2009 | Fisker |
| 2009/0220917 A1 | 9/2009 | Jensen |
| 2009/0239197 A1 | 9/2009 | Brajnovic |
| 2009/0239200 A1 | 9/2009 | Brajnovic |
| 2009/0253097 A1 | 10/2009 | Brajnovic |
| 2009/0263764 A1 | 10/2009 | Berckmans, III |
| 2009/0287332 A1 | 11/2009 | Adusumilli |
| 2009/0298009 A1 | 12/2009 | Brajnovic |
| 2009/0298017 A1 | 12/2009 | Boerjes |
| 2009/0317763 A1 | 12/2009 | Brajnovic |
| 2009/0325122 A1 | 12/2009 | Brajnovic |
| 2010/0009314 A1 | 1/2010 | Tardieu |
| 2010/0028827 A1 | 2/2010 | Andersson |
| 2010/0038807 A1 | 2/2010 | Brodkin |
| 2010/0075275 A1 | 3/2010 | Brajnovic |
| 2010/0092904 A1 | 4/2010 | Esposti |
| 2010/0105008 A1 | 4/2010 | Powell |
| 2010/0173260 A1 | 7/2010 | Sogo |
| 2010/0280798 A1 | 11/2010 | Pattijn |
| 2011/0008751 A1 | 1/2011 | Pettersson |
| 2011/0060558 A1 | 3/2011 | Pettersson |
| 2011/0111371 A1* | 5/2011 | Haber ............... A61C 1/084 433/201.1 |
| 2011/0129792 A1 | 6/2011 | Berckmans, III |
| 2011/0183289 A1 | 7/2011 | Powell |
| 2011/0191081 A1 | 8/2011 | Malfliet |
| 2011/0200970 A1* | 8/2011 | Berckmans, III .... A61C 8/0001 433/180 |
| 2011/0244426 A1 | 10/2011 | Amber |
| 2011/0269104 A1 | 11/2011 | Berckmans, III |
| 2011/0275032 A1 | 11/2011 | Tardieu |
| 2011/0300509 A1 | 12/2011 | Dadi |
| 2011/0306008 A1 | 12/2011 | Suttin |
| 2011/0306009 A1 | 12/2011 | Suttin |
| 2012/0010740 A1 | 1/2012 | Swaelens |
| 2012/0164593 A1 | 6/2012 | Bavar |
| 2012/0164893 A1 | 6/2012 | Misuzuka |
| 2012/0251979 A1 | 10/2012 | Karim |
| 2012/0282567 A1 | 11/2012 | Nilsson |
| 2012/0295223 A1 | 11/2012 | Robb |
| 2012/0295226 A1 | 11/2012 | Robb |
| 2013/0196290 A1 | 8/2013 | Herrington |
| 2013/0289950 A1* | 10/2013 | Kopelman ......... A61C 13/0004 703/1 |
| 2014/0080092 A1 | 3/2014 | Suttin |
| 2014/0080095 A1 | 3/2014 | Suttin |
| 2014/0162214 A1 | 6/2014 | Jansen |
| 2015/0173862 A1 | 6/2015 | Suttin et al. |

FOREIGN PATENT DOCUMENTS

| | | |
|---|---|---|
| DE | 4028855 A1 | 3/1992 |
| DE | 10029256 | 11/2000 |
| EP | 0442855 A1 | 8/1991 |
| EP | 0583829 A1 | 2/1994 |
| EP | 0657146 A1 | 6/1995 |
| EP | 0727193 A1 | 8/1996 |
| EP | 0747017 A2 | 12/1996 |
| FR | 2759896 A3 | 8/1998 |
| GB | 1291470 A | 10/1972 |
| JP | 59/151344 | 10/1984 |
| JP | 63/169115 | 11/1988 |
| JP | H05/212063 A | 8/1993 |
| JP | H06/154252 A | 6/1994 |
| JP | H09/218916 A | 8/1997 |
| WO | WO 85/02337 A1 | 6/1985 |
| WO | WO 94/26200 | 11/1994 |
| WO | WO 99/32045 | 7/1999 |
| WO | WO 00/08415 | 2/2000 |
| WO | WO 01/34057 A1 | 5/2001 |
| WO | WO 01/58379 | 8/2001 |
| WO | WO 02/053055 | 7/2002 |
| WO | WO 03/024352 | 3/2003 |
| WO | WO 2004/030565 | 4/2004 |
| WO | WO 2004/075771 | 9/2004 |
| WO | WO 2004/087000 | 10/2004 |
| WO | WO 2004/098435 | 11/2004 |
| WO | WO 2005/023138 | 3/2005 |
| WO | WO 2006/014130 | 2/2006 |
| WO | WO 2006/062459 | 6/2006 |
| WO | WO 2006/082198 | 8/2006 |
| WO | WO 2007/005490 | 1/2007 |
| WO | WO 2007/033157 | 3/2007 |
| WO | WO 2007/062658 | 6/2007 |
| WO | WO 2007/104842 | 9/2007 |
| WO | WO 2007/129955 | 11/2007 |
| WO | WO 2008/057955 | 5/2008 |
| WO | WO 2008/083857 | 7/2008 |
| WO | WO 2009/146164 | 12/2009 |
| WO | WO 2012/158769 | 11/2012 |
| WO | WO 2014/043036 | 3/2014 |

OTHER PUBLICATIONS

"International Application Serial No. PCT/US2014/068634, International Preliminary Report on Patentability mailed Jun. 30, 2016", 13 pgs.

"International Application Serial No. PCT/US2014/068637, International Preliminary Report on Patentability mailed Jun. 30, 2016", 8 pgs.

3Shape, 3Shape Dental System, "Digitally moving the world of dentistry," 52 pages, dated 2012.

3Shape, Implant Studio, "Implant Planning and Surgical Guide Design," 7 pages, dated 2015.

Biomet 3i & Sirona, "Improve your workflow and patient treatment process," 2 pages, dated Feb. 2013.

Biomet 3i, "Navigator™ System for CT Guided Surgery Manual", 34 pages, dated Oct. 2007.

Francois Goulette et al., "A New Method and a Clinical Case for Computer Assisted Dental Implantology," 7 pages, dated Sep. 6, 2003, Retrieved from Summer European university in surgical Robotics at URL:www.lirmm.fr/manifs/UEE/docs/students/goulette.pdf.

International Search Report for International Application No. PCT/US2014/068634, 2 pages, dated Mar. 10, 2015.

International Search Report for International Application No. PCT/US2014/068637, 4 pages, dated Apr. 16, 2015.

Jakob Brief et al., "Accuracy of image-guided implantology," 7 pages, Aug. 20, 2004, Retrieved from Google, <URL:sitemaker.umich.edu/sarmentlab/files/robodent_vs_denx_coir_05.pdf.

MediNEWS.Direct!. "'Surgical Glue' May Help to Eliminate Suturing for Implants," 1 page, Dec. 21, 2007, Retrieved from MediNEWS.Direct, URL:http://www.medinewsdirect.com/?p=377.

"Robots are ready for medical manufacturing," 7 pages, Jul. 12, 2007, Retrieved from MachineDesign.Com, <URL: http://machinedesign.com/article/robots/are/ready/for/medical/manufacturing/0712>.

Sirona, "Cerec in Practice: Clinically Secure," 2 pages, date unknown.

Sirona, "Sirona Dental CAD/CAM System ScanPost," Operating Instructions, 10 pages, Mar. 2013.

Sirona, Integrated Implantology, "The Digital Workflow With Sirona," 7 pages, date unknown.

Sirona, Sirona Connect, "Join Us in the World of Digital Impressions," 13 pages, date unknown.

(56) References Cited

OTHER PUBLICATIONS

Written Opinion for International Application No. PCT/US2014/068634, 11 pages, dated Mar. 10, 2015.
Written Opinion for International Application No. PCT/US2014/068637, 6 pages, dated Apr. 16, 2015.
Zebra Technologies Corporation, "The Basics of Bar Coding," Application Whitepaper, 20 pages, date unknown.

* cited by examiner

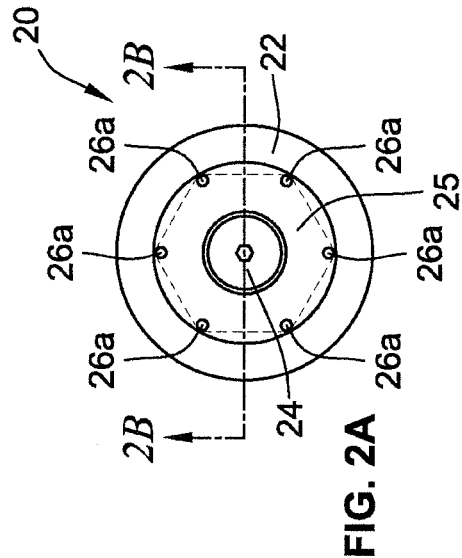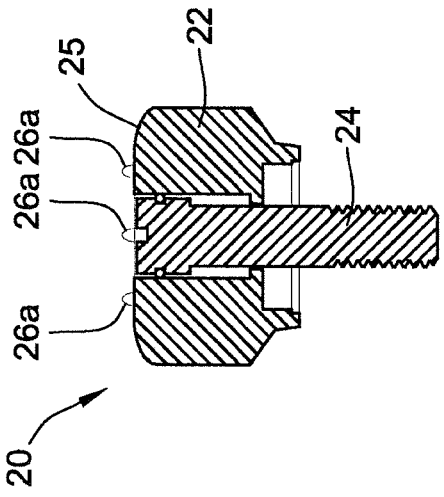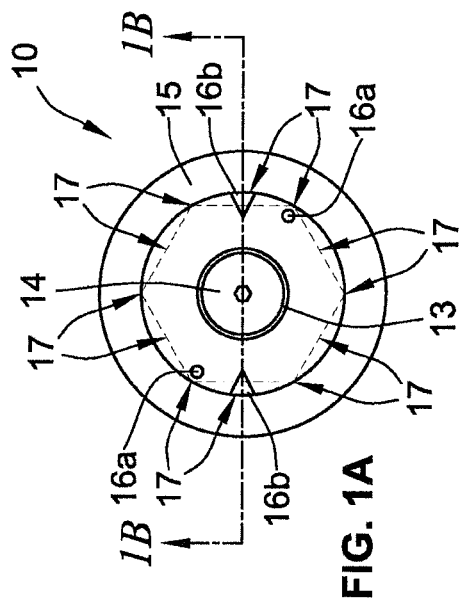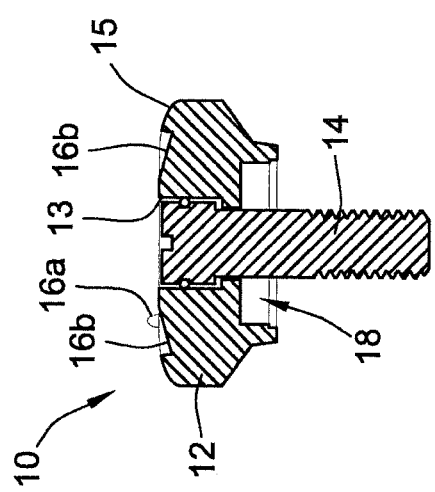
FIG. 1A FIG. 2A
FIG. 1B FIG. 2B

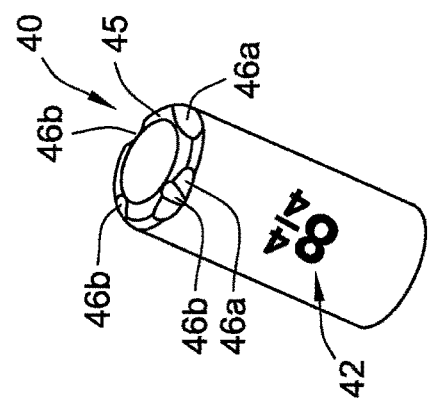
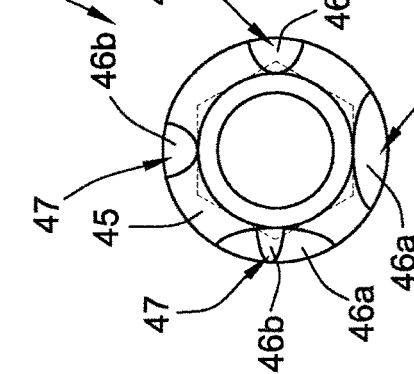
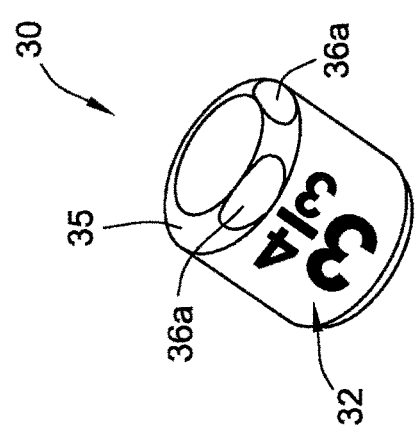
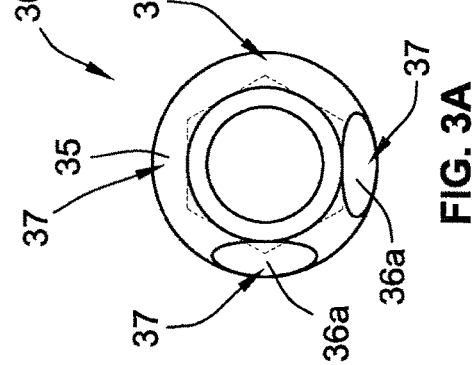
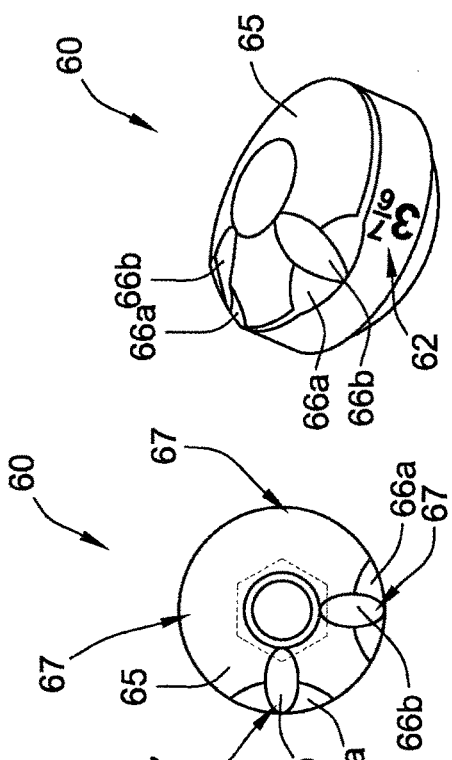
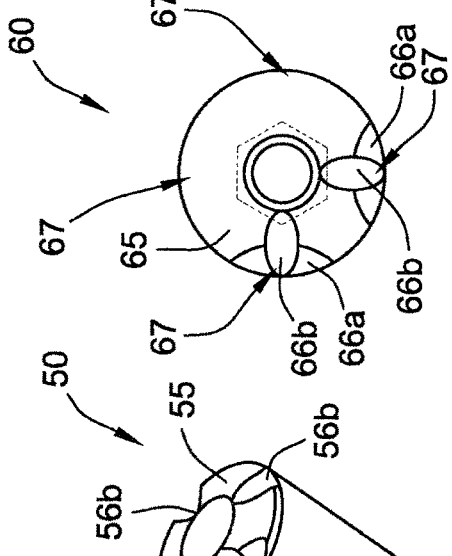
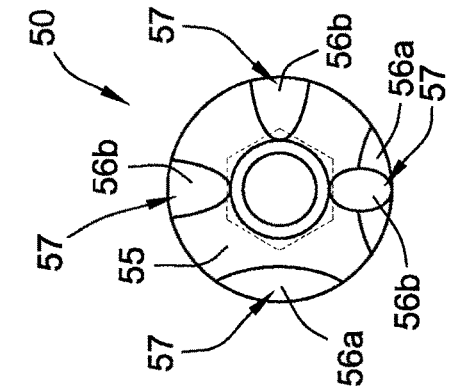

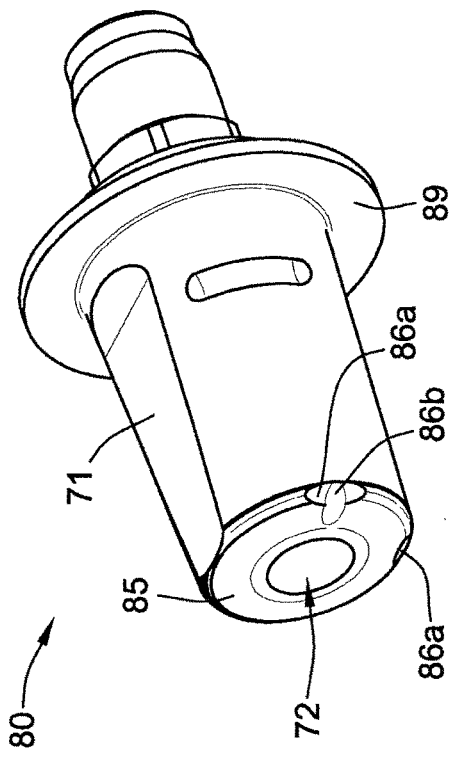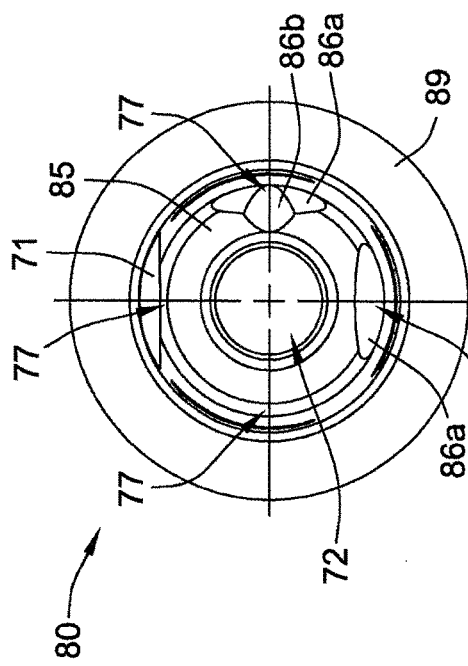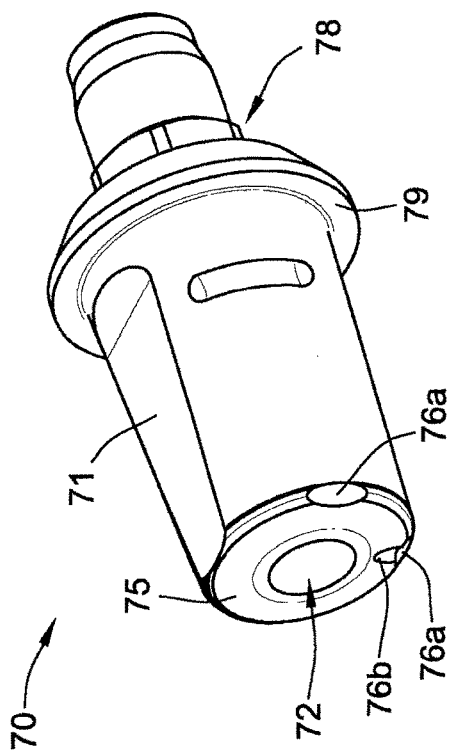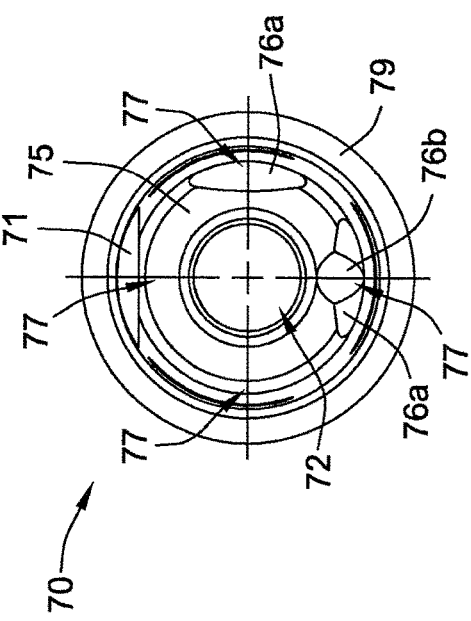

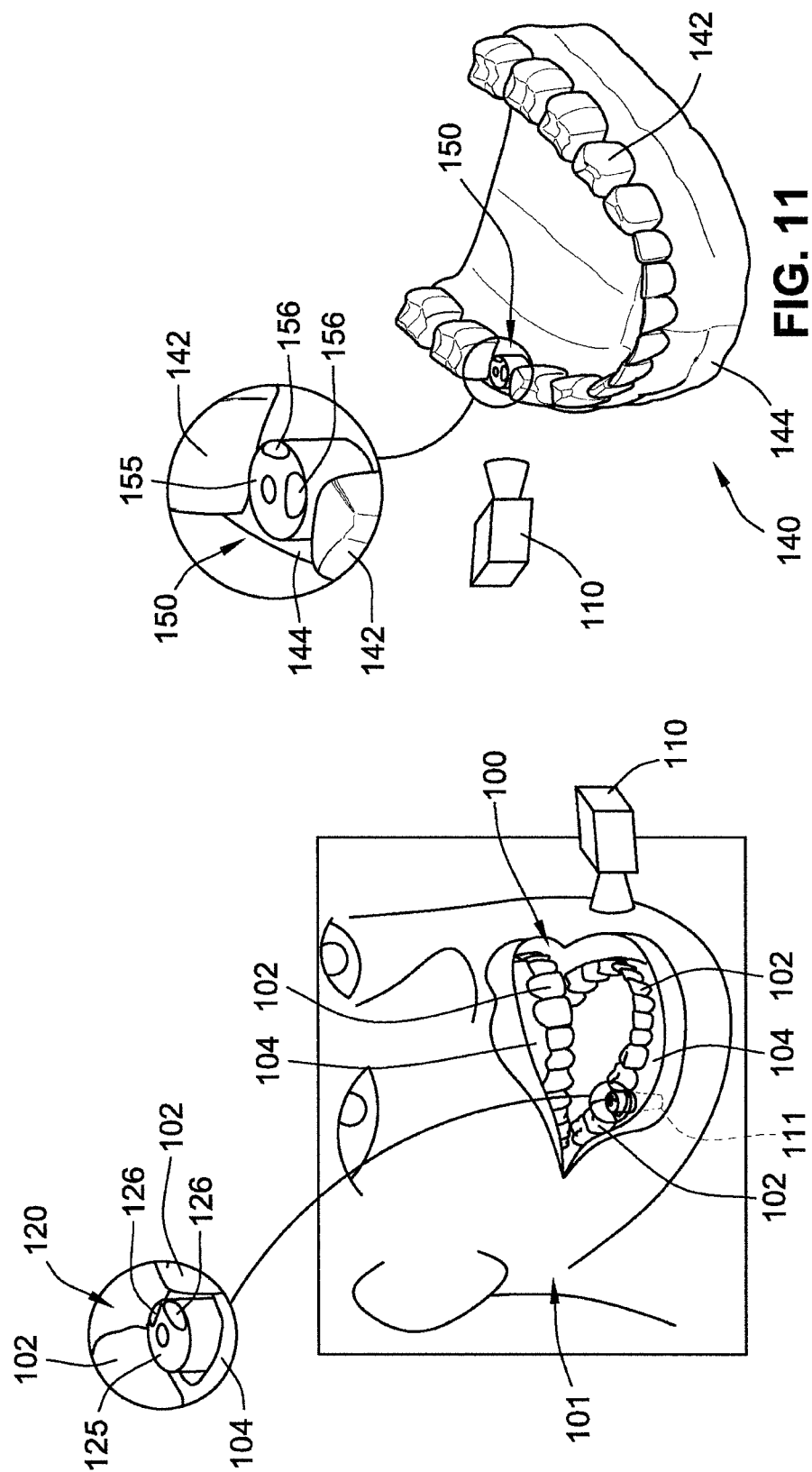

INPUT

OUTPUT

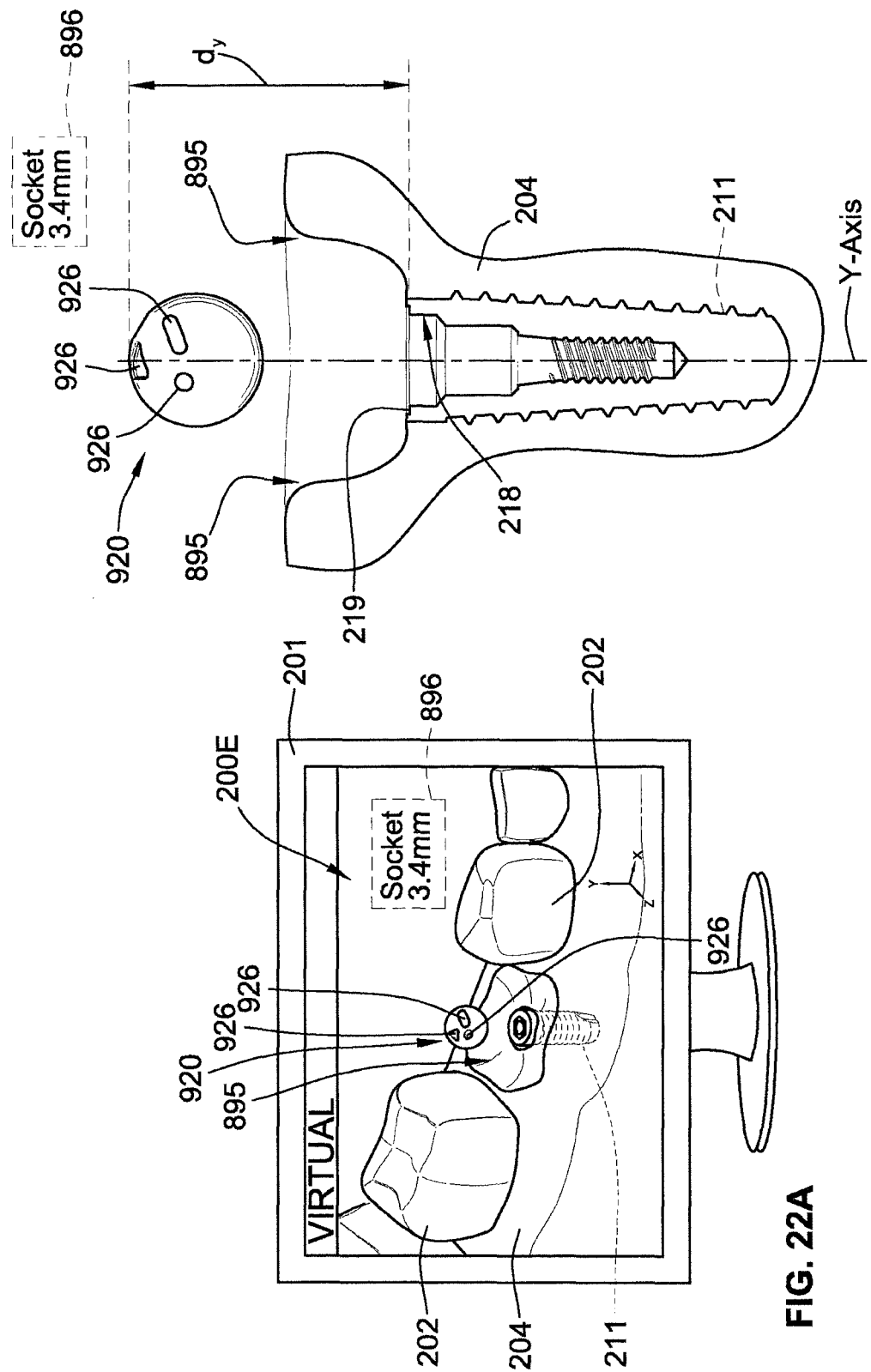

DENTAL SYSTEM FOR DEVELOPING CUSTOM PROSTHESES THROUGH SCANNING OF CODED MEMBERS

CROSS REFERENCE TO RELATED APPLICATIONS

This application claims the benefit of U.S. Provisional Application No. 61/991,964, filed May 12, 2014, and U.S. Provisional Application No. 61/918,987, filed Dec. 20, 2013, each of which is hereby incorporated by reference herein in its entirety.

FIELD OF THE INVENTION

The present disclosure relates generally to a dental implant system. More particularly, the present disclosure relates to a dental implant system for developing custom prostheses through scanning of coded members.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, in the form of a dental implant, is placed in the jawbone for osseointegration. The dental implant generally includes a threaded bore to receive a retaining screw for holding mating components thereon. During the first stage, the gum tissue overlying the implant is sutured and heals as the osseointegration process continues.

Once the osseointegration process is complete, the second stage is initiated. Here, the gingival tissue is re-opened to expose an end of the dental implant. A healing component or healing abutment is fastened to the exposed end of the dental implant to allow the gingival tissue to heal therearound. It should be noted that the healing abutment can be placed on the dental implant immediately after the implant has been installed and before osseointegration. In recent years, for some situations, the osseointegration step and gingival healing steps have been combined into a one-step process.

Further, in recent years, scanning technology has been used to identify the conditions in the patient's mouth adjacent to a dental implant by scanning the patient's mouth with a scannable healing abutment or another scanning member installed on the implant. Alternatively, an impression may be taken of the patient's mouth, and the scan is taken of the impression or a stone model created from the impression. Ultimately, the data from these various scans is used to create a model that is used to develop a custom prosthesis for attachment to the patient's dental implant.

In one exemplary healing abutment system, informational markers or codes are located on a top surface of the healing abutments. The informational markers can be used to identify information about the specific healing abutment (e.g., the orientation of its non-rotational feature, the dimensions of the healing abutment, etc.). Thus, each healing abutment has exactly one specific code on the top surface. Once the code for that healing abutment is identified (e.g., using scanning techniques), the size (e.g., platform diameter, emergence-profile shape, maximum body diameter, height, overall external geometry, etc.) of that healing abutment can be determined by reference to a library that correlates the code and the specific healing abutment. This library is relatively small (e.g., less than 50 codes, less than 40 codes, less than 30 codes, etc.) as each specific size of healing abutment has a single code. For example, a healing abutment having a 3.4 mm platform diameter, a 3.8 mm maximum body diameter, and a 3 mm height always has the same code represented on the top surface thereof using, for example, one or more informational markers in the shape of notches. Thus, if a manufacturer only sells healing abutments in ten different sizes, then only ten codes are needed to be placed on corresponding top surfaces of the healing abutments for use in identifying the ten different healing abutments. Once the size information and the orientation information of the healing abutment are obtained using the library, a location and orientation of an underlying implant attached to the healing abutment can be determined, which is needed for development of patient-specific components to be attached to the implant. In essence, the codes provide information about the implant and the shape of the opening in the gingival tissue leading to the implant. This type of system is generally described in U.S. Pat. No. 6,790,040, assigned to the assignee of the present disclosure, which is hereby incorporated by reference herein in its entirety.

In one exemplary system, a temporary healing component is scanned prior to being placed in the mouth of a patient and then scanned after being attached to an implant in the mouth of the patient. Such scans are then used to develop an implant level three-dimensional model of the patient's dental conditions for use in designing and/or fabricating a final prosthesis. However, the scanning of the temporary healing component has some drawbacks as compared with the use of codes thereon to develop the three-dimensional model as the level of captured details of the scanned temporary healing component are limited by the ability of the scanner.

SUMMARY OF THE INVENTION

The present invention in many ways is the antithesis of the above-described methodology related to prior art healing abutment and scanning systems. Specifically, the present disclosure provides for multiple codes (not a single code) to identify the same size of healing abutment or other scannable member, which makes it more difficult for unscrupulous competitive entities to identify and copy the codes for healing abutments. Thus, for a specific size of healing abutment or a healing abutment having a specific geometrical configuration (e.g., a healing abutment having a non-standard and/or a non-round shape), multiple codes can be placed on those healing abutments. For example, a first healing abutment having a 3.4 mm platform diameter, a 3.8 mm maximum body diameter, and a 3.0 mm height (referred to as a 343 healing abutment) has a first code on its top surface and a second healing abutment also having a 3.4 mm platform diameter, a 3.8 mm maximum body diameter, and a 3.0 mm height has a second code, different than the first code, on its top surface. That is, the first and the second healing abutments are substantially identical, except for the different codes on their respective top surfaces. However, both of the first and the second codes correlate to the same "343" healing abutment having the same 3.4 mm platform diameter, a 3.8 mm maximum body diameter, and a 3.0 mm height. In such an example, a non-public code-to-abutment correlation library, preferably maintained in secret by the manufacturer of the healing abutments and/or a trusted third party, includes the first code and the second code and a correlation for both the first and the second codes to the 343 healing abutment. Thus, the non-public code-to-abutment library could be used to identify the first and the second healing abutments as 343 healing abutments using the first and the second codes. However, when a large set of healing abutments is available and each healing abutment within the set has multiple codes, it becomes much more difficult for an unscrupulous third party to correlate the codes to the specific healing abutment. In summary, the present disclosure provides healing abutments of the same size with different codes on top surfaces thereof—the antithesis of the prior art. Further, the present invention not only applies to healing abutments that can be scanned, but other types of dental-implant attachment components that can be used in conjunction with a scanning process to develop a custom prosthesis.

To make it even more difficult for unscrupulous third parties to identify the codes and their corresponding size of healing abutments, the codes on the different sizes of healing abutments can be changed randomly and/or changed at specific times. For example, every six months or so, the code or codes used for identifying the 343 healing abutment can be changed, and such a change would only be known to the keeper of the non-public code-to-abutment correlation library. Such a scheme of changing codes on healing abutments can be referred to as a rolling-code system.

As the non-public code-to-abutment correlation library of the present disclosure is maintained in secrecy, customers (e.g., dentists, oral surgeons, etc.) that use the healing abutments of the present disclosure are encouraged to seek out the manufacturer and/or a trusted third party to decode the code using the non-private code-to-abutment correlation library as such information is needed to develop the patient-specific custom components (e.g., patient specific crown, patient-specific abutment, etc.) for the patient. To do so, the customer sends scan data (usually in the form of a virtual healing abutment surface within a virtual model of a patient's mouth) to the manufacturer and/or a trusted third party. The code on the virtual healing abutment is located within the scan data and is identified to provide a correlation to a specific size healing abutment. A publicly available virtual "proxy abutment" having a known proxy code then replaces the virtual healing abutment within the virtual model. The virtual proxy abutment allows third parties (e.g., dental laboratories) without access to the non-public code-to-abutment correlation library to determine the location and orientation of the underlying implant and/or additional information related to the virtual proxy abutment and/or the replaced virtual healing abutment (e.g., platform diameter, emergence profile shape, maximum body diameter, height, overall external geometry, etc.), which is needed for that third party to develop a patient-specific prosthesis for use on the implant installed in the patient's mouth. In summary, the virtual proxy abutment, which has publicly known information, is usable by the customers and other third parties in this type of dental system to develop the patient—specific prosthesis. Yet, the non-public code-to-abutment correlation library can be maintained by the manufacturer and/or a trusted third party.

According to some implementations of the present disclosure, a method for developing a patient-specific prosthesis to be coupled to an implant installed in a mouth of a patient includes scanning a scanning member that is attached to the implant to obtain scan data. The scanning member has a top surface with a code thereon. The code is indicative of a size of the scanning member and an orientation of a non-rotational fitting of the scanning member. From the scan data, a virtual three-dimensional model of the mouth is created. The virtual three-dimensional model includes a virtual scanning member with a virtual code thereon. The virtual code corresponds to the code on the scanning member attached to the implant in the mouth of the patient. The virtual code associated with the virtual scanning member is obtained from the virtual three-dimensional model. Based on a scanning-member library, the size of the scanning member is determined from the virtual code. Based on the virtual code, the orientation of the non-rotational fitting of the scanning member is determined. The virtual scanning member in the virtual three-dimensional model is replaced with a virtual proxy abutment to create a modified virtual three-dimensional model. The virtual proxy abutment has known characteristics for determining (i) an orientation for the patient-specific prosthesis to be attached to the implant and (ii) a size of at least a portion of the patient-specific prosthesis. The patient-specific prosthesis to be coupled to the implant in the mouth of the patient is designed by use of the virtual proxy abutment. The virtual proxy abutment provides the same information as the coded healing abutment, which can then be utilized to design the patient-specific prosthesis.

According to some implementations of the present disclosure, a set of healing abutments includes a first healing abutment and a second healing abutment. The first healing abutment has an upper surface with a first code thereon. The first code is associated with a size of the first healing abutment. The second healing abutment has an upper surface with a second code thereon. The second code is associated with a size of the second healing abutment. The first healing abutment and the second healing abutment have the same size. The first code is different from the second code.

According to some implementations of the present disclosure, a set of scanning members includes a first scanning member and a second scanning member. The first scanning member has a first code on an outer surface thereof. The first code is indicative of a size of the first scanning member. The second scanning member has a second code on an outer surface thereof. The second code is indicative of a size of the second scanning member. The first scanning member has the same size as the second scanning member and the first code is different from the second code.

According to some implementations of the present disclosure, a system for use in developing a patient-specific prosthesis to be coupled to an implant installed in a mouth of a patient includes a plurality of healing abutments and a storage medium. The plurality of healing abutments includes at least a first healing abutment and a second healing abutment that are intended to be scanned, while in the mouth, to create a virtual model. The first healing abutment has a top surface with a first code thereon. The first code is at least associated with a height of the first healing abutment. The second healing abutment has a top surface with a second code thereon. The second code is at least associated with a height of the second healing abutment. The height of the first healing abutment is different from the height of the second healing abutment and the first code is different from the second code. The storage medium is associated with the plurality of healing abutments and stores executable instructions configured, upon execution by one or more processors, to cause the system to (i) identify whether the virtual model includes virtual features indicative of the first code or the second code, (ii) alter the virtual model to include a first virtual proxy abutment if the first code is present, and (iii) alter the virtual model to include a second virtual proxy abutment if the second code is present.

According to some implementations of the present disclosure, a method for developing a patient-specific prosthesis to be coupled to an implant installed in a mouth of a patient includes scanning a scanning member that is attached to the implant to obtain scan data. The scanning member has a code thereon. The code is indicative of a size of the scanning member and an orientation of a non-rotational fitting of the scanning member. Within a virtual three-dimensional model of the mouth created using the scan data, a first virtual proxy abutment to be added to the virtual three-dimensional model is selected if the code is a first code. The first virtual proxy abutment has a first set of known characteristics for determining (i) an orientation for the patient-specific prosthesis to be coupled to the implant and (ii) a size of at least a portion of the patient-specific prosthesis. Within the virtual three-dimensional model of the mouth created using the scan data, a second virtual proxy abutment to be added to the virtual three-dimensional model is selected if the code is a second code. The second virtual proxy abutment has a second set of known characteristics that is different from the first set of known characteristics. The patient-specific prosthesis to be coupled to the implant in the mouth of the patient is designed by use of either the first virtual proxy abutment or the second virtual proxy abutment.

According to some implementations of the present disclosure, a method for developing a patient-specific prosthesis to be coupled to an implant installed in a mouth of a patient includes non-rotationally attaching a healing abutment to the implant. The healing abutment has a code thereon. The code is associated with a size of the healing abutment. After a sufficient period of time during which gingival tissue surrounding the healing abutment has healed, at least a portion of the mouth including the healing abutment is scanned to create a virtual three-dimensional model of at least a portion of the mouth. The virtual three-dimensional model includes a portion of a virtual healing abutment having a virtual code thereon. The virtual code corresponds to the code on the healing abutment attached to the implant in the mouth of the patient. The virtual three-dimensional model is transmitted from a first party to a second party. The second party has access to a code-to-abutment correlation library and the first party does not having access to the code-to-abutment correlation library. Code information associated with the code on the healing abutment is obtained from the transmitted virtual three-dimensional model. The obtained code information and the code-to-abutment correlation library is used to determine (i) a size of the healing abutment and (ii) an orientation of the healing abutment. A virtual proxy abutment is selected using the determined size of the healing abutment and a proxy abutment correlation library. The transmitted virtual three-dimensional model is modified to remove the portion of the virtual healing abutment and to include the virtual proxy abutment. The virtual proxy abutment is positioned in the modified virtual three-dimensional model at a position and orientation associated with the location and the orientation of the portion of the virtual healing abutment in the transmitted virtual three-dimensional model. The modified virtual three-dimensional model is transmitted from the second party to a third party. A proxy code associated with the virtual proxy abutment is obtained from the transmitted modified virtual three-dimensional model. The obtained proxy code is used to determine information related to the virtual proxy abutment. A patient-specific prosthesis to be coupled to the implant in the mouth of the patient is designed based on the information determined from the proxy code.

According to some implementations of the present disclosure, a system for use in developing a patient-specific prosthesis to be coupled to an implant installed in a mouth of a patient includes a plurality of scanning members and a storage medium. The plurality of scanning members are intended to be scanned, while in the mouth, to create a virtual model. The plurality of scanning members include a first set of scanning members and a second set of scanning members. Each of the scanning members in the first set of scanning members has (i) a different height and (ii) a code from a first set of codes thereon. Each code in the first set of codes is different. Each of the scanning members in the second set of scanning members has (i) a different height and (ii) a code from a second set of codes thereon. Each code in the second set of codes is different. The storage medium is associated with the plurality of scanning members and stores executable instructions configured, upon execution by one or more processors, to cause the system to (i) identify whether the virtual model includes virtual features indicative of one of the codes in the first set of codes or one of the codes in the second set of codes, (ii) alter the virtual model to include a first proxy abutment if one of the first set of codes is present, and (iii) alter the virtual model to include a second proxy abutment if one of the second set of codes is present.

According to some implementations of the present disclosure, a plurality of scanning members that are attachable to a dental implant installed in a patient's mouth include a first set of scanning members and a second set of scanning members. The first set of scanning members has a first set of codes on outer surfaces thereof. Each of the first set of codes is indicative of a size of the corresponding one of the first set of scanning members. The first set of scanning members includes scanning members of different sizes. The second set of scanning members has a second set of codes on outer surfaces thereof. Each of the second set of codes is indicative of a size of the corresponding one of the second set of scanning members. The second set of scanning members includes scanning members of different sizes. A presence of one of the first set of codes in a virtual model of the patient's mouth results in the virtual model being modified to include a first virtual proxy abutment and a presence of one of the second set of codes in the virtual model of the patient's mouth results in the virtual model being modified to include a second virtual proxy abutment. The first virtual proxy abutment is different from the second virtual proxy abutment. Each of the first and the second virtual proxy abutments has characteristics used in developing a patient-specific prosthesis to be attached to the dental implant.

According to some implementations of the present disclosure, a method for developing a patient-specific prosthesis to be coupled to an implant installed in a mouth of a patient includes scanning a scanning member that is attached to the implant to obtain scan data. The scanning member has a top surface with a code thereon. The code is indicative of a size of the scanning member and an orientation of a non-rotational fitting of the scanning member. From the scan data, a virtual three-dimensional model of the mouth is created. The virtual three-dimensional model includes a virtual scanning member with a virtual code thereon. The virtual code corresponds to the code on the scanning member attached to the implant in the mouth of the patient. From the virtual three-dimensional model, the virtual code associated with the virtual scanning member is obtained. Based on a scanning-member library, the size of the scanning member is determined from the virtual code. Based on the virtual code, the orientation of the non-rotational fitting of the scanning member is determined. The virtual scanning member is replaced in the virtual three-dimensional model with a virtual gingival aperture and a virtual proxy abutment to create a modified virtual three-dimensional model. The virtual gingival aperture corresponds to a size of at least a portion of the scanning member. The virtual proxy abutment has known characteristics for determining a location and an orientation for the patient-specific prosthesis to be attached to the implant. By use of the virtual gingival aperture and the virtual proxy abutment, the patient-specific prosthesis to be coupled to the implant in the mouth of the patient is designed.

According to some implementations of the present disclosure, a method for developing a patient-specific prosthesis to be coupled to an implant installed in a mouth of a patient includes modifying a virtual three-dimensional model including one or more virtual teeth, virtual gingival tissue, and a virtual scanning member. The modifying includes replacing the virtual scanning member with a virtual gingival aperture and a floating virtual proxy abutment to create a modified virtual three-dimensional model. The floating virtual proxy abutment is virtually detached from the rest of the modified virtual three-dimensional model and the floating virtual proxy abutment has known characteristics for determining a location and an orientation for a virtual implant to be positioned in the modified virtual three-dimensional model that corresponds with the position and orientation of the implant in the mouth of the patient. By use of the virtual gingival aperture and the positioned virtual implant, the patient-specific prosthesis to be coupled to the implant in the mouth of the patient is designed.

According to some implementations of the present disclosure, a virtual three-dimensional model for use in developing a patient-specific prosthesis to be coupled to an implant installed in a mouth of a patient includes one or more virtual teeth, virtual gingival tissue, and a floating virtual proxy abutment. The virtual gingival tissue includes a virtual gingival aperture leading to a location for a virtual implant. The floating virtual proxy abutment is positioned relative to the virtual gingival aperture and is virtually detached from the rest of the virtual three-dimensional model. The floating virtual proxy abutment has known characteristics for determining a location and an orientation for the patient-specific prosthesis to be attached to the implant.

According to some implementations of the present disclosure, a system for use in developing a patient-specific prosthesis to be coupled to an implant installed in a mouth of a patient includes a scanning member and a storage medium. The scanning member is a member of a set of scanning members and is intended to be scanned while in the mouth to create a virtual model. Each of the scanning members in the set of scanning members has (i) a different height and (ii) a code from a set of codes thereon. Each code in the set of codes is different. The storage medium is associated the set of scanning members and stores executable instructions configured, upon execution by one or more processors, to cause the system to (i) identify whether the virtual model includes virtual features indicative of one of the codes in the set of codes and (ii) alter the virtual model to include a first virtual proxy abutment if one of codes in the set of codes is present.

BRIEF DESCRIPTION OF THE DRAWINGS

The foregoing and other advantages of the invention will become apparent upon reading the following detailed description and upon reference to the drawings.

FIG. 1A is a top view of a healing abutment with a first coding system according to some implementations of the present disclosure;

FIG. 1B is a cross-sectional side view of the healing abutment shown in FIG. 1A;

FIG. 2A is a top view of a second healing abutment with the first coding system according to some implementations of the present disclosure;

FIG. 2B is a cross-sectional side view of the second healing abutment shown in FIG. 2A;

FIG. 3A is a top view of a third healing abutment with a second coding system that is different from the first coding system relative to FIGS. 1A-2B;

FIG. 3B is a perspective view of the third healing abutment shown in FIG. 3A;

FIG. 4A is a top view of another healing abutment with the second coding system;

FIG. 4B is a perspective view of the healing abutment shown in FIG. 4A;

FIG. 5A is a top view of yet another healing abutment with the second coding system;

FIG. 5B is a perspective view of the healing abutment shown in FIG. 5A;

FIG. 6A is a top view of a further healing abutment with the second coding system;

FIG. 6B is a perspective view of the healing abutment shown in FIG. 6A;

FIG. 7A is a top view of a temporary abutment having a coding system;

FIG. 7B is perspective view of the temporary abutment shown in FIG. 7A;

FIG. 8A is a top view of a second temporary abutment having the coding system;

FIG. 8B is perspective view of the temporary abutment shown in FIG. 8A;

FIG. 10 illustrates a scanning device that directly scans a portion of a mouth of a patient for use in creating a virtual three-dimensional model;

FIG. 11 illustrates a scanning device that scans a stone model of a mouth of a patient for use in creating a virtual three-dimensional model;

FIG. 22A illustrates a perspective view of the modified virtual three-dimensional model of FIG. 20 having a floating virtual proxy abutment virtually detached from and positioned relative to the surrounding portion of the modified virtual three-dimensional model according to some implementations of the present disclosure; and FIG. 22B illustrates a partial cross-sectional view of the modified virtual three-dimensional model of FIG. 22A.

Figure 9:
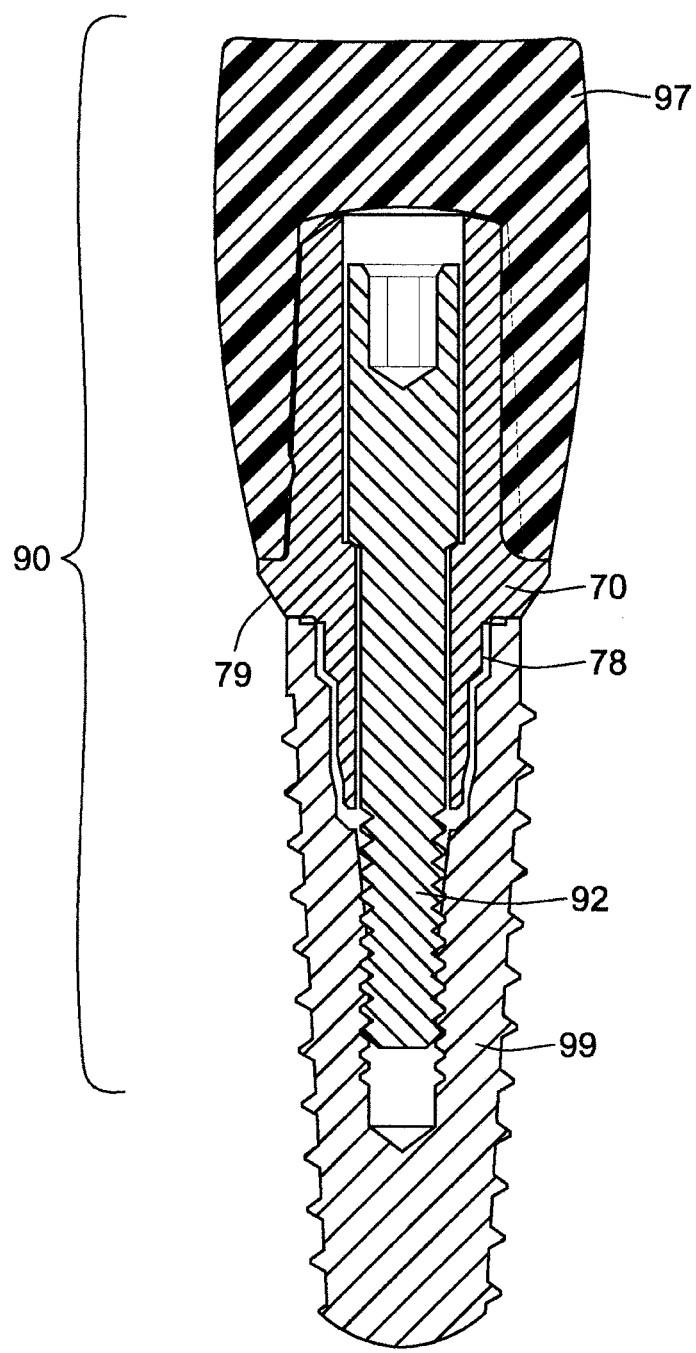
FIG. 9 is a cross-sectional side view of a temporary prosthesis coupled to an implant via the temporary abutment of FIGS. 7A and 7B according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE IMPLEMENTATIONS

Referring to FIGS. 1A and 1B, a two-piece healing abutment 10 includes an abutment body 12 (FIG. 1B) and a retaining screw 14. The abutment body 12 is generally cylindrical in shape with an internal bore 13 for receiving the retaining screw 14 to removably couple the healing abutment 10 to an implant (not shown) installed in a mouth of a patient. As shown in FIG. 1B, the abutment body 12 includes a female anti-rotational feature 18 (e.g., a hexagonal socket) suitable for mating in a non-rotational manner with an implant (not shown) having a corresponding anti-rotational male feature (e.g., a hexagonal boss). Of course, the male/female anti-rotational features can be reversed where the healing abutment includes a male anti-rotational feature (e.g., a hexagonal boss) and the implant includes a female anti-rotational feature (e.g., a hexagonal socket).

A top surface 15 of the abutment body 12 includes two types of informational markers 16a, 16b at certain ones of a plurality of informational marker locations 17. As shown in FIG. 1A, there are twelve informational marker locations 17, including six informational marker locations 17 located generally above the six corners of the underlying female anti-rotational feature 18 (e.g., a hexagonal socket) and the other six informational markers 17 located generally above the six flats of the underlying female anti-rotational feature 18 (e.g., a hexagonal socket). While twelve informational marker locations 17 are shown and described, any other number of informational marker locations 17 are possible (e.g., two informational marker locations, four informational marker locations, six informational marker locations, etc.). Each of the informational marker locations 17 on the healing abutment 10 is configured to include one or more informational markers, and the presence or absence of such markers provides information.

The informational markers 16a, 16b are indicative of one or more characteristics of the healing abutment 10 itself and/or of the underlying implant (not shown) to which the healing abutment 10 is attached. The presence, absence, size, and/or shape of the first informational markers 16a at certain marker locations 17 can correspond to the height of the healing abutment 10 and, hence, a height or vertical position (i.e., z-axis location) of a table or seating surface of the underlying implant. Or, the presence, absence, size, and/or shape of the first informational markers 16a can be indicative of the x-y location of the table or seating surface of the underlying implant. In another example, the first informational markers 16a can be indicative of the angle that the underlying implant rests with respect to vertical within the patient's jawbone (e.g., pitch and yaw). In a further example, the presence, absence, size, and/or shape of the first informational markers 16a can be indicative of the size and/or shape of the healing abutment 10 and/or the underlying implant and/or provide information indicative of the manufacturer of the underlying implant. The second type of informational markers 16b can be indicative of other information. For example, the second type of informational markers 16b can be geometrically aligned with opposing flats of the anti-rotational feature 18 of the healing abutment 10 (and, thus, the flat surfaces on the underlying implant's anti-rotational feature) to indicate the rotational orientation of the non-rotational features of the healing abutment 10 and the underlying implant.

As best shown in FIG. 1B, the first information markers 16a are shown as pimples or small projections from the top surface 15 in predefined informational marker locations 17 (e.g., informational marker locations that are equally spaced around the top surface 15 and corresponding to the corners of the underlying female anti-rotational feature 18). The second information markers 16b are shown as divots or notches in the top surface 15 in predefined informational marker locations 17 (e.g., informational marker locations that are equally spaced around the top surface 15 and corresponding to the locations of the flats of the underlying female anti-rotational feature 18). The presence and/or absence of an informational marker or code in an informational marker location 17 provides information about the size of the healing abutment 10, the orientation of the healing abutment 10 relative to an underlying implant (e.g., the orientation of the flats of the underlying anti-rotational feature 18 relative to the flats of the underlying implant), and/or the contours of the sub-gingival tissue that abuts the healing abutment 10, which are not exposed (e.g., the sub-gingival tissue is assumed/predicted to heal around the contours of the healing abutment 10 and thus takes the shape of the contours of the healing abutment 10).

The informational markers 16a, 16b can be positive informational markers (such as raised projections/pimples), negative informational markers (such as indentations, notches, or dimples), lines, etching, alphanumeric characters, etc. It is further contemplated that the cross-section of the informational markers can be shaped a certain way, such as rectangles, triangles, or various other shapes. Further, the informational marker locations 17 themselves can act as informational markers and provide and/or indicate information (e.g., orientation of an underlying socket or boss).

According to some implementations, the informational markers 16a, 16b define a binary marking system that identifies unique characteristics of the healing abutment 10 and/or the underlying implant. As is well known, a binary-coded system exists as an array of digits, where the digits are either "1" or "0" that represent two states, respectively, ON and OFF. For each informational marker location 17, the presence of an informational marker 16a, 16b ("ON") is a 1 and the absence of an informational marker 16a, 16b ("OFF") is a 0. By grouping sets of 1's and 0's together starting from a known starting location, a code for the healing abutment is determined (e.g., 1-0-0-1 for a four informational marker location healing abutment, 0-0-1-0-0-1-1-1-0-0 for a ten informational marker location healing abutment, etc.), and using that code (e.g., with reference to a non-public code-to-abutment correlation library), information about each healing abutment 10 can be determined. In this type of binary-coded system, one or more markings (e.g., a notch, a line, an arrow, etc.) are typically present to indicate the first "digit" to be read in a certain order across the top surface 15 of the healing abutment 10, such as clockwise or counterclockwise.

In short, the combination of the informational markers 16a, 16b and the informational marker locations 17 on the top surface 15 of the abutment body 12 form a code. As such, the set of informational markers 16a, 16b (and other informational markers described herein) can be referred to as a code. The code for any given dental-implant component (e.g., healing abutment, temporary abutment, etc.) can be interpreted with reference to a non-public code-to-abutment correlation library (which is described in more detail below) to determine a size and/or an orientation of the component and, thus, information related to the underlying implant and gingival aperture leading to the implant. Further, in lieu of using informational markers, such as, for example, notches and/or protrusions to define a code that is used in identifying a healing abutment, the code for a particular healing abutment can be a known preformed shape and/or a known geometry on a top surface of the healing abutment that is identifiable by scanning the top surface. For example, the code can be a single wave on the top surface, two waves, a random structure that is identical from abutment to abutment of the same size, etc. For another example, the code can include a dot, a dash, a triangle, a square, a circle, an oval, or any combination thereof, printed on and/or etched into a surface (e.g., a top surface) of the healing abutment.

Additional information on informational markers and/or codes and/or informational marker locations is found in U.S. Pat. No. 6,790,040 and U.S. Pat. App. Pub. No. 2012-0295223, both of which are assigned to the assignee of the present disclosure and are hereby incorporated by reference herein in their entireties.

Referring to FIGS. 2A and 2B, another two-piece healing abutment 20 includes an abutment body 22 and a retaining screw 24. The healing abutment 20 is similar to the healing abutment 10 of FIGS. 1A and 1B. However, the healing abutment 20 has a different size (e.g., relatively larger height than the healing abutment 10) and a different code on a top surface 25 thereof. Specifically, the top surface 25 of the abutment body 22 includes informational markers 26a that define the code. The informational markers 26a are similar to the informational markers 16a in that the informational markers 26a are in the form of pimples or small projections from the top surface 25 of the abutment body 22. However, the informational markers 26a are different from the informational markers 16a, 16b, and define a different code, which identifies the healing abutment 20 relative to other healing abutments (including the healing abutment 10). The code from the informational markers 26a for can be interpreted with reference to a non-public code-to-abutment correlation library to determine a size and/or an orientation of the healing abutment 20 and, thus, the information related to the underlying implant and gingival aperture leading to the implant.

Referring to FIGS. 3A-6B, different codes on different healing abutments 30, 40, 50, and 60 help to identify each one of the healing abutments. The four two-piece healing abutments 30, 40, 50, and 60 (the screw pieces are not shown) have different sizes, as shown in FIGS. 3A-6B. Specifically, FIGS. 3A and 3B show a "343" healing abutment 30 having a 3.4 mm platform diameter (for mating with the implant), a 3.8 mm maximum body diameter, and a 3.0 mm height. FIGS. 4A and 4B show a "448" healing abutment 40 having a 4.1 mm platform diameter, a 4.1 mm maximum body diameter, and an 8.0 mm height. FIGS. 5A and 5B show a "568" healing abutment 50 having a 5.0 mm platform diameter, a 6.0 mm maximum body diameter, and an 8.0 mm height. FIGS. 6A and 6B show a "673" healing abutment 60 having a 6.0 mm platform diameter, a 7.5 mm maximum body diameter, and a 3.0 mm height. The healing abutments 30, 40, 50, and 60 may include indicium 32, 42, 52, and 62 that provides these various dimensions. But even when included, the indicium 32, 42, 52, and 62 on the sides of each respective healing abutment 30, 40, 50, and 60 are typically obscured (partially or completely) when the healing abutments 30, 40, 50, and 60 are installed in a mouth of a patient. In such instances, reliance on the codes (e.g., determined by the informational markers and the informational marker locations) disposed on the respective top surfaces 35, 45, 55, and 65 of the healing abutments 30, 40, 50, and 60 is necessary to: (i) determine the size of the healing abutment and (ii) determine the orientation of the healing abutment's non-rotational feature that will mate with the underlying implant.

For example, as shown best in FIG. 3A, the top surface 35 of the abutment 30 includes a first set of informational markers 36a, which define the orientation of the underlying anti-rotational feature that mates with the implant. As will be discussed below, each of other three healing abutments 40, 50, 60 in FIGS. 4-6 also includes a similar first set of informational markers for defining the orientation of the underlying anti-rotational feature. The first set of informational markers 36a are shown as relatively large/wide notches positioned in two separate and adjacent quarters of the top surface 35.

In the case of the healing abutment 30 (as well as healing abutments 40, 50, 60 in FIGS. 4-6), the top surface 35 is divided into four information marker locations 37, two of which overlap with the two informational markers in the first set of informational markers 36a. Each of the four information marker locations 37 includes or lacks a second type of informational marker. On the healing abutment 30, the top surface 35 includes none of a second type of informational markers at the four information marker locations 37. With no second type of informational markers at the four information marker locations 37, if using a binary system, the code of the healing abutment 30 would be 0-0-0-0. The code of the abutment 30 is preferably interpreted or decoded relative to the orientation of the first set of informational markers 36a

(or some other structure) on the healing abutment 30 (e.g., starting at six o'clock where the rightmost first type of information marker 36a is present and moving clockwise). The code on the top surface 35 of the healing abutment 30 can be interpreted or decoded with reference to a non-public code-to-abutment correlation library to identify the abutment 30 (including its size and dimensions) with knowledge only of the code on the top surface 35 (e.g., not with knowledge of the indicia 32 "343" on the side of the healing abutment 30, which is likely obscured when installed). While four informational marker locations 37 are shown, the number of informational marker locations 37 can be varied (e.g., two locations, five locations, six locations, ten locations, twelve locations, etc.).

In FIGS. 4A and 4B, a top surface 45 of the abutment 40 includes four informational marker locations 47, two of the first type of informational markers 46a, and three of the second type of informational markers 46b. The first type of informational markers 46a is the same as, or similar to, the first type of informational markers 36a described in reference to FIG. 3A in that they establish the location of the underlying non-rotational feature. The second type of informational markers 46b are shown as relatively small notches positioned in three of the four informational marker locations 47 of the top surface 45. One of the second types of informational markers 46b coincides with one of the first type of informational markers 46a such that they overlap. If using a binary system, starting at six o'clock at the rightmost first type of information marker 46a and moving clockwise, the code of the healing abutment 40 would be 0-1-1-1 as defined by the presence or absence of the second type of informational markers 46b in the four informational marker locations 47. Thus, the information markers 46a and 46b on the top surface 45 provides a code for identifying the healing abutment 40 and locating its underlying anti-rotational feature that mates with the implant. The code on the top surface 45 can be interpreted or decoded with reference to the non-public code-to-abutment correlation library to identify the abutment 40 with knowledge only of the code on the top surface 45 (e.g., not with knowledge of the indicia 42 on the side of the healing abutment 40, which is likely obscured when installed).

As shown in FIGS. 5A and 5B, a top surface 55 of the abutment 50 includes four informational marker locations 57, two of the first type of informational markers 56a, and three of the second type of informational markers 56b. The first type of informational markers 56a is the same as, or similar to, the first type of informational markers 36a described in reference to FIG. 3A in that they establish the location of the underlying non-rotational feature. The second type of informational markers 56b are shown as relatively small notches positioned in three of the four informational marker locations 57 of the top surface 55. One of the second type of informational markers 56b coincides with one of the first type of informational markers 56a such that they overlap. If using a binary system, starting at six o'clock at the rightmost first type of information marker 56a and moving clockwise, the code of the healing abutment 50 would be 1-0-1-1 as defined by the presence or absence of the second type of informational markers 56b in the four informational marker locations 57. The information markers 56a and 56b on the top surface 55 provides a code for identifying the healing abutment 50 and locating its underlying anti-rotational feature that mates with the implant. The code on the top surface 55 can be interpreted or decoded with reference to the non-public code-to-abutment correlation library to identify the abutment 50.

Similarly, in FIGS. 6A and 6B, a top surface 65 of the abutment 60 includes informational marker locations 67, the first type of informational markers 66a, and the second type of informational markers 66b. The same system described above with reference to FIGS. 3A-5B is present. If using a binary system, and starting at six o'clock at the rightmost first type of information marker 66a and moving clockwise, the code of the healing abutment 60 would be 1-1-0-0 as defined by the presence or absence of the second type of informational markers 66b in the four informational marker locations 67. The information markers 66a and 66b on the top surface 65 provides a code for identifying the healing abutment 60 and for locating the orientation of the underlying anti-rotational feature that mates with the implant. The code on the healing abutment 60 be interpreted or decoded with reference to the non-public code-to-abutment correlation library.

As shown in FIGS. 3A-6B, the codes on the top surfaces 35, 45, 55, and 65 are different, which indicates that the healing abutments 30, 40, 50, and 60 each have different sizes. Of course, as described in further detail below, according to the present disclosure, different codes on two healing abutments does not necessarily mean that the two healing abutments have different sizes because multiple codes can be used to indicate the same size healing abutment.

While the healing abutments 10, 20, 30, 40, 50, and 60 have been described as being a part of sets of healing abutments having an identifiable marking system (e.g., a binary marking system), the actual codes (e.g., 1-0-1-1 or 0-0-1-1) may not necessarily be required for identification of each type of abutment. Rather, shape-matching algorithms within the software used to analyze the virtual models having virtual healing abutments that have been produced by a scanning process can be used to identify the type of healing abutment within the virtual model.

It should also be understood that the size of the maximum body diameter of the healing abutment relative to the diameter of the screw hole is also useful for identifying a specific healing abutment through the scanning process. For example, it is possible to use the same code on two different sized healing abutments, because the relative diametric sizes of the two different healing abutments can identify the healing abutment even when the same code is used.

Further, although the healing abutments 10, 20, 30, 40, 50, and 60 have been described relative to a four-digit binary code system (e.g., 1-0-1-1, 0-0-1-1, etc.), one pair of informational marker locations 17, 27, 37, 47, 57, 67 can be used to indicate one specific characteristic, while a second pair of marking locations 17, 27, 37, 47, 57, 67 can be used to indicate another specific characteristic of the healing abutment. As an example, and with reference to FIGS. 6A and 6B, the presence or absence of the second type of informational markers 66b at six o'clock and/or at nine o'clock (i.e., within the regions of the first type of informational markers 66a that indicates the orientation of the underlying implant) can dictate one of four possible platform diameters (e.g., implant diameters), such as 3.4 mm, 4.1 mm, 5.0 mm, and 5.5 mm. And, the presence or absence of the second type of informational markers 66b at twelve o'clock and/or at three o'clock (i.e., opposite the regions of the first type of informational markers 66a that indicate the orientation of the underlying implant) can dictate one of four possible healing abutment heights, such as 3.0 mm, 4.0 mm, 6.0 mm, and 8.0 mm. In other words, the informational marker locations on the top surface of the healing abutment can be divided into groups (e.g., two groups) and certain characteristics of the healing abutment can be associated with each group. The maximum body diameter of the healing abutment can be gauged by the overall width of the upper surface that is found from the scan. Again, if the diameter of the screw hole is a constant in all sizes of implants, determining the size of the overall diameter (e.g., maximum body diameter) of the healing abutment can be readily obtained because of a known and scalable feature (e.g., the diameter of the screw hole) on the upper surface of the healing abutment. Similarly, a known and scaled line can be placed on the upper surfaces of each healing abutment for scaling purposes.

The type of screw that is placed within the opening of a healing abutment can also provide information. For example, the head of the screw that is generally coplanar with the upper surface of the healing abutment can have one or more features (e.g., grooves) to indicate the type of implant connection, such as an internally hexed implant (i.e., an implant with an internal hexagonal socket) versus an externally hexed implant (i.e., an implant with an external hexagonal boss)

In addition to informational markers and codes being used with healing abutments (e.g., the healing abutments 10, 20, 30, 40, 50, and 60), informational markers and codes can be used on other types of components used in conjunction with dental implants. For example, temporary abutments used in temporary prostheses can include codes for identifying the size of the temporary abutment and/or an orientation of the temporary abutment. For example, as shown in FIGS. 7A and 7B, a temporary abutment 70 has a generally cylindrical shape with an internal bore 72 for receiving a screw 92 (shown in FIG. 9) for removably coupling the temporary abutment 70 to an implant 99 (shown in FIG. 9). A top surface 75 of the temporary abutment 70, which is best shown in FIG. 7A, includes four informational marker locations 77. The informational marker locations 77 are positioned circumferentially around the top surface 75 of the temporary abutment 70. While the temporary abutment 70 is shown with informational marker locations 77 at locations of 3 o'clock, 6 o'clock, 9 o'clock, and 12 o'clock, with respect to an anti-rotational structure 71 being at 12 o'clock, it is contemplated that additional informational marker locations (not shown) can be located on the top surface 75 (e.g., between 9 o'clock and 12 o'clock, between 3 o'clock and 6 o'clock, etc.).

The top surface 75 of the temporary abutment 70 includes four informational marker locations 77, two informational markers 76a, and one informational marker 76b. The informational markers 76a are the same as, or similar to, the informational markers 36a described in reference to FIG. 3A and the informational markers 76b are the same as, or similar to, the informational markers 46b described in reference to FIG. 4A. The informational markers 76a, the informational markers 76b, and the informational marker locations 77 provided a code for identifying the temporary abutment 70 and locating its underlying anti-rotational feature 78 (shown in FIG. 7B) of the temporary abutment 70.

Similarly, in FIGS. 8A and 8B, a temporary abutment 80 includes all of the same features as the temporary abutment 70. However, the temporary abutment 80 has a different size. The difference is noticeable in that the temporary abutment 80 has a relatively wider flange 89 than a flange 79 (FIG. 7B) of the temporary abutment 70. The top surface 85 of the temporary abutment 80 includes a different code defined by informational markers 86a and informational markers 86b, which indicates that the temporary abutment 80 has at least one characteristic that is different from the temporary abutment 70. In short, other components beyond healing abutments can include codes that can be picked up through scans.

Referring to FIG. 9, an assembled view of a temporary prosthesis assembly 90 and a dental implant 99 is shown. The prosthesis assembly 90 includes the temporary abutment 70 and a temporary prosthesis 97 coupled to the temporary abutment 70 providing a temporary tooth. The implant 99 is installed in a jawbone (not shown) of a patient, and then the temporary abutment 70 is non-rotationally attached to the implant 99 via the underlying anti-rotational feature 78 (best shown in FIG. 7B) and the screw 92. The temporary abutment 70 is attached to the implant 99 such that a bottom portion of the flange 79 of the temporary abutment 70 abuts and/or rests upon a table or seating surface of the dental implant 99. Additional details on the temporary prosthesis assembly 90 and other similar assemblies including temporary abutments with informational markers and informational marker locations can be found in U.S. Pat. App. Pub. No. 2012-0295223, assigned to the assignee of the present disclosure, which is hereby incorporated by reference herein in its entirety.

With the above details about coded dental implant components in mind, the following disclosure is generally directed towards methods of creating virtual three-dimensional models of at least a portion of a mouth of a patient for use in developing custom components to be attached to an implant in the mouth of the patient (e.g., patient-specific abutments, patient specific crowns, etc.). As a brief overview of some of the disclosed methods of the present disclosure, an implant is installed in the mouth of a patient. Either at the time of installation of the implant or after an osseointegration period, a healing abutment (e.g., healing abutment 10, 20, 30, 40, 50, 60) is attached to the implant in a non-rotational manner. That healing abutment has a top surface with a code thereon (e.g., one or more informational markers positioned in one or more informational marker locations). Immediately after installation of the healing abutment and/or after a healing period where the gingival tissue is permitted to heal around the healing abutment, a virtual three-dimensional model of at least a portion of the mouth of the patient is created using one or more scanning techniques.

The virtual three-dimensional model having the virtual healing abutment with the coded top surface is sent to an authorized entity (e.g., the manufacturer of the healing abutments or its authorized licensee or agent) installed in the patient's mouth. The authorized agent analyzes the virtual three-dimensional model and, specifically, the portion depicting the top surface of the healing abutment having the code for the healing abutment (e.g., using at least one computer executing one or more software programs that preferably include shape-matching algorithms). With reference to a non-public (i.e., private) code-to-abutment correlation library accessible by the authorized entity, the authorized entity identifies the particular healing abutment and its size (e.g., a "343" healing abutment) using the code on the upper top surface. The authorized entity, using the code, also determines an orientation of the anti-rotational feature of the healing abutment.

Figure 13:
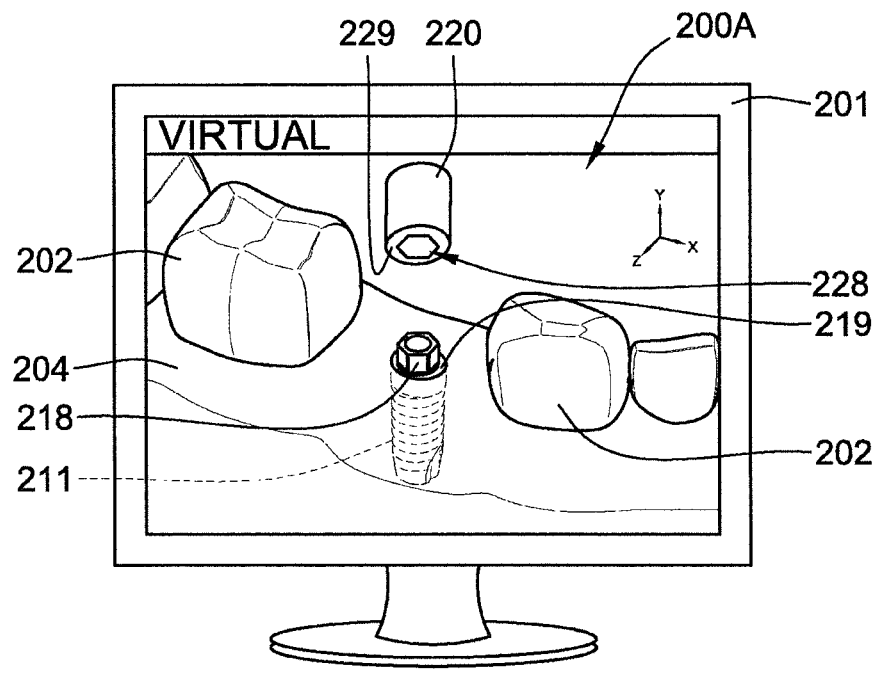
FIG. 13 illustrates a modified virtual three-dimensional model of the mouth of the patient where the virtual healing abutment of FIG. 12 has been removed, and a virtual proxy abutment is provided to fit on a virtual implant.
Figure 14:
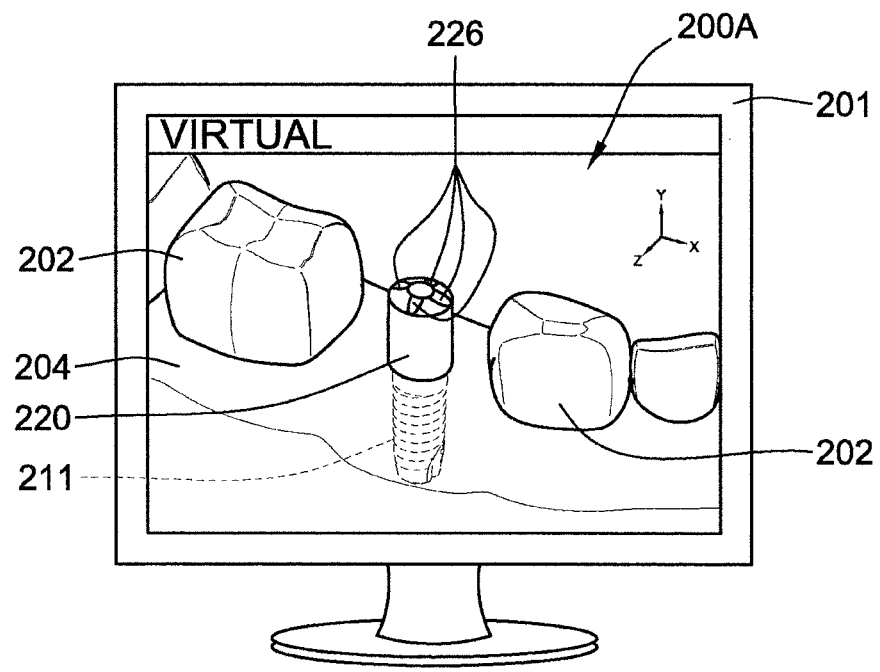
FIG. 14 illustrates the modified virtual three-dimensional model of FIG. 13 where the virtual proxy abutment is attached to the virtual implant.
Figures 21A, 21B:
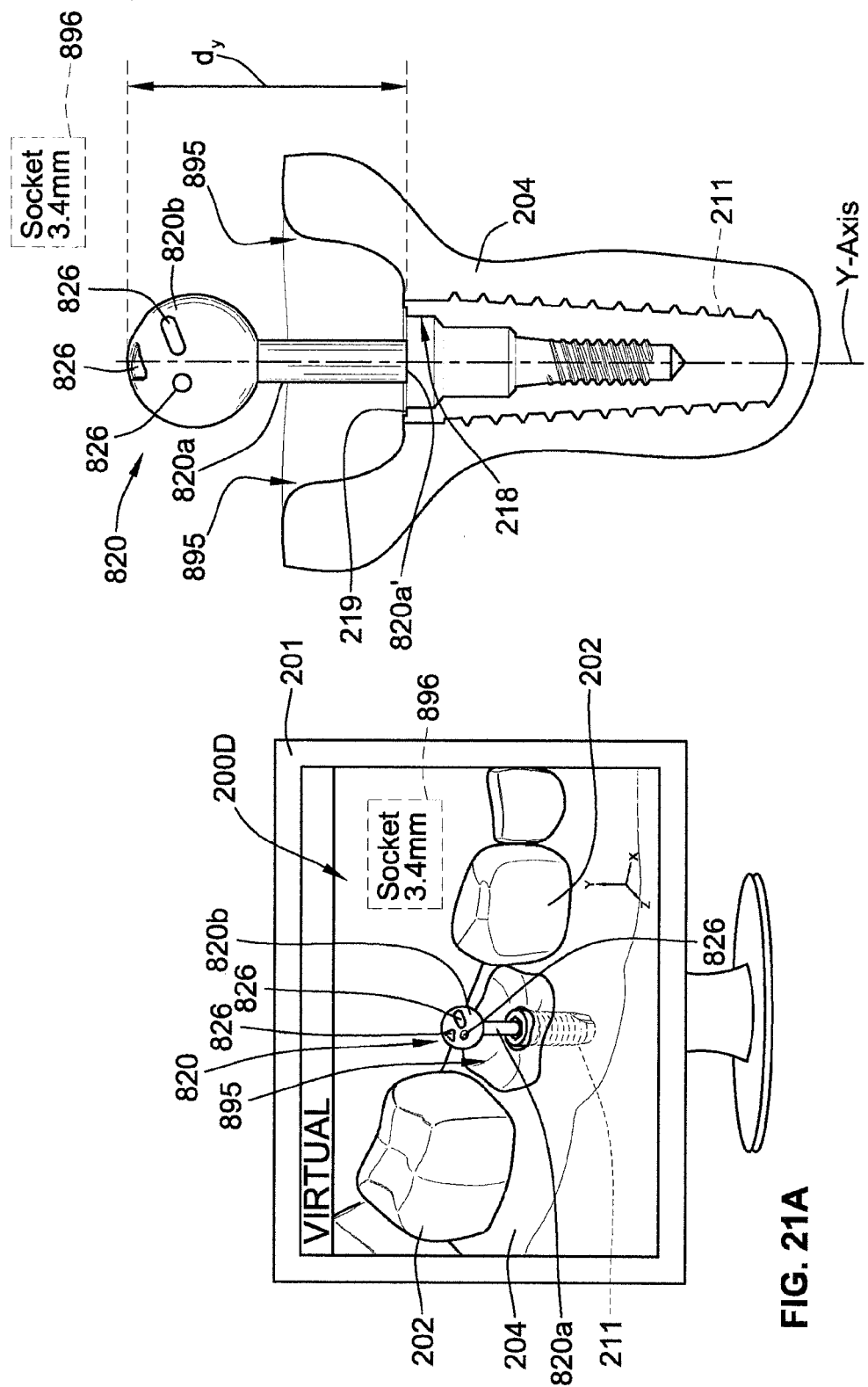
FIG. 21A illustrates a perspective view of the modified virtual three-dimensional model of FIG. 20 having a narrow virtual proxy abutment contiguous with the surrounding portion of the modified virtual three-dimensional model according to some implementations of the present disclosure.
FIG. 21B illustrates a partial cross-sectional view of the modified virtual three-dimensional model of FIG. 21A.

With the determined size and orientation, the authorized entity then modifies the virtual three-dimensional model by removing the virtual healing abutment and replacing it with a virtual proxy abutment (e.g., virtual proxy abutment 220 shown in FIGS. 13 and 14, narrow virtual proxy abutment 820 shown in FIGS. 21A and 21B, floating virtual proxy abutment 920 shown in FIGS. 22A and 22B, etc.). The virtual proxy abutment has a surface (e.g., a top or upper surface) with a virtual proxy code located thereon. After the virtual three-dimensional model is modified to include the virtual proxy abutment, the authorized entity sends the modified virtual three-dimensional model to another party (e.g., a dental laboratory) that uses the modified virtual three-dimensional model to develop the patient-specific components for the patient. The virtual proxy abutment has a publicly known size and shape that is correlated to its virtual proxy code. Thus, this modification by the authorized entity essentially replaces the healing abutment with a virtual proxy abutment. As such, to develop the pertinent components (e.g., permanent and/or temporary patient-specific abutment, permanent and/or temporary patient-specific crown, etc.), the other party receiving the modified virtual three-dimensional model only needs to have knowledge of a publicly available proxy abutment library and not the non-public code-to-abutment and/or abutment-to-proxy correlation libraries.

A more specific description of the above summarized method is provided with reference to FIGS. 10-17B. Starting with FIG. 10, a mouth 100 of a patient 101 having a healing abutment 120 installed therein is created by scanning the mouth 100 using a scanner 110 (e.g., an intraoral scanner/camera). The mouth 100 of the patient 101 includes teeth 102, gingival tissue 104, a dental implant 111, and the healing abutment 120 coupled to the dental implant 111. As shown in FIG. 10, while the implant 111 is in the mouth 100, the implant 111 is located within the bone and is hidden from view, except that the upper surface of the implant 111 could be seen below the healing abutment 120 if the healing abutment 120 is detached from the implant 111.

Figures 16A, 16B:
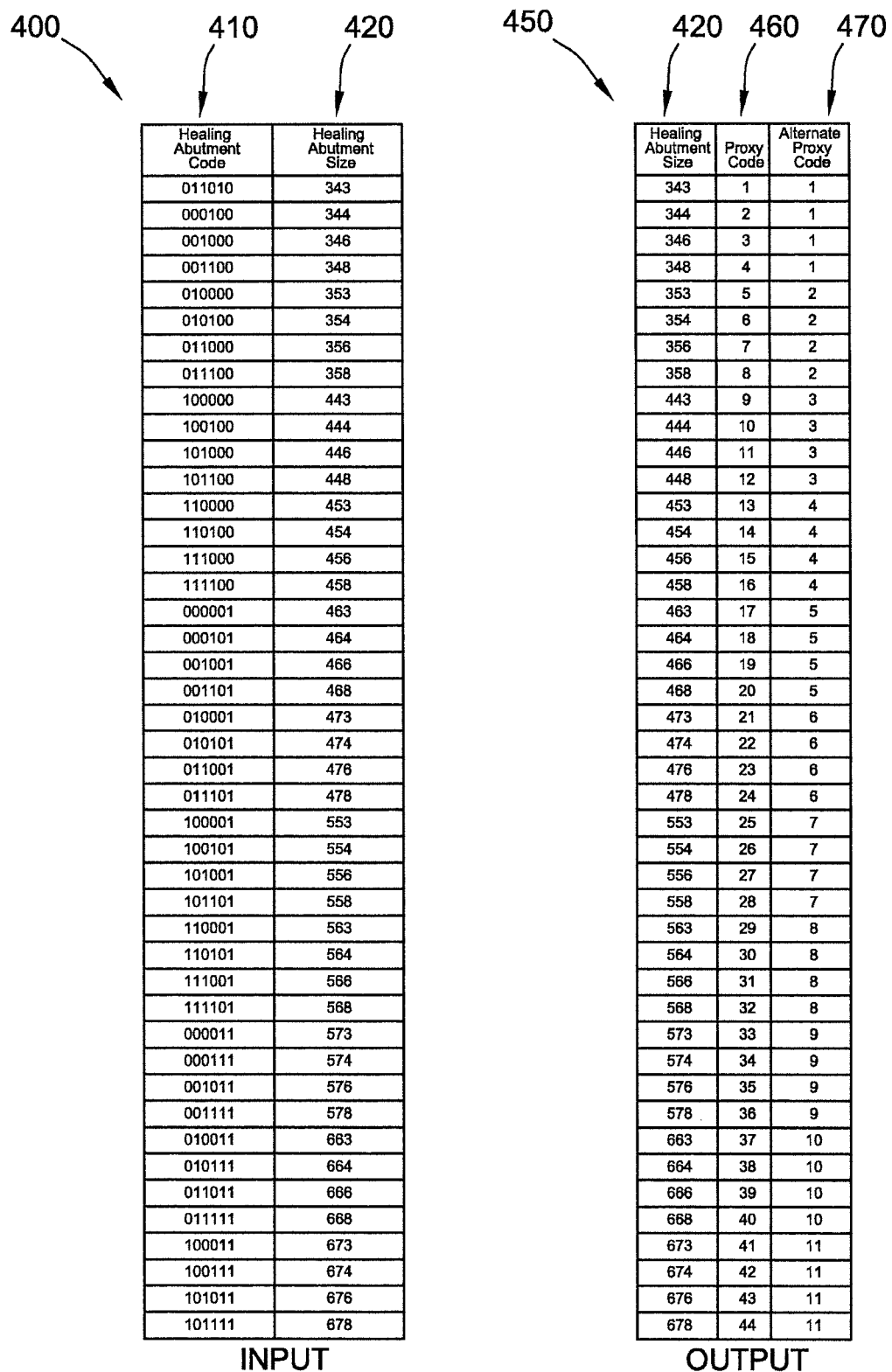
FIG. 16A is a non-public code-to-abutment correlation library illustrating codes that correlate to specific sizes of healing abutments according to some implementations of the present disclosure.
FIG. 16B is a non-public abutment-to-proxy correlation library illustrating virtual proxy abutments that correlate to the specific sizes of healing abutments of FIG. 16A.
Figures 17A, 17B:
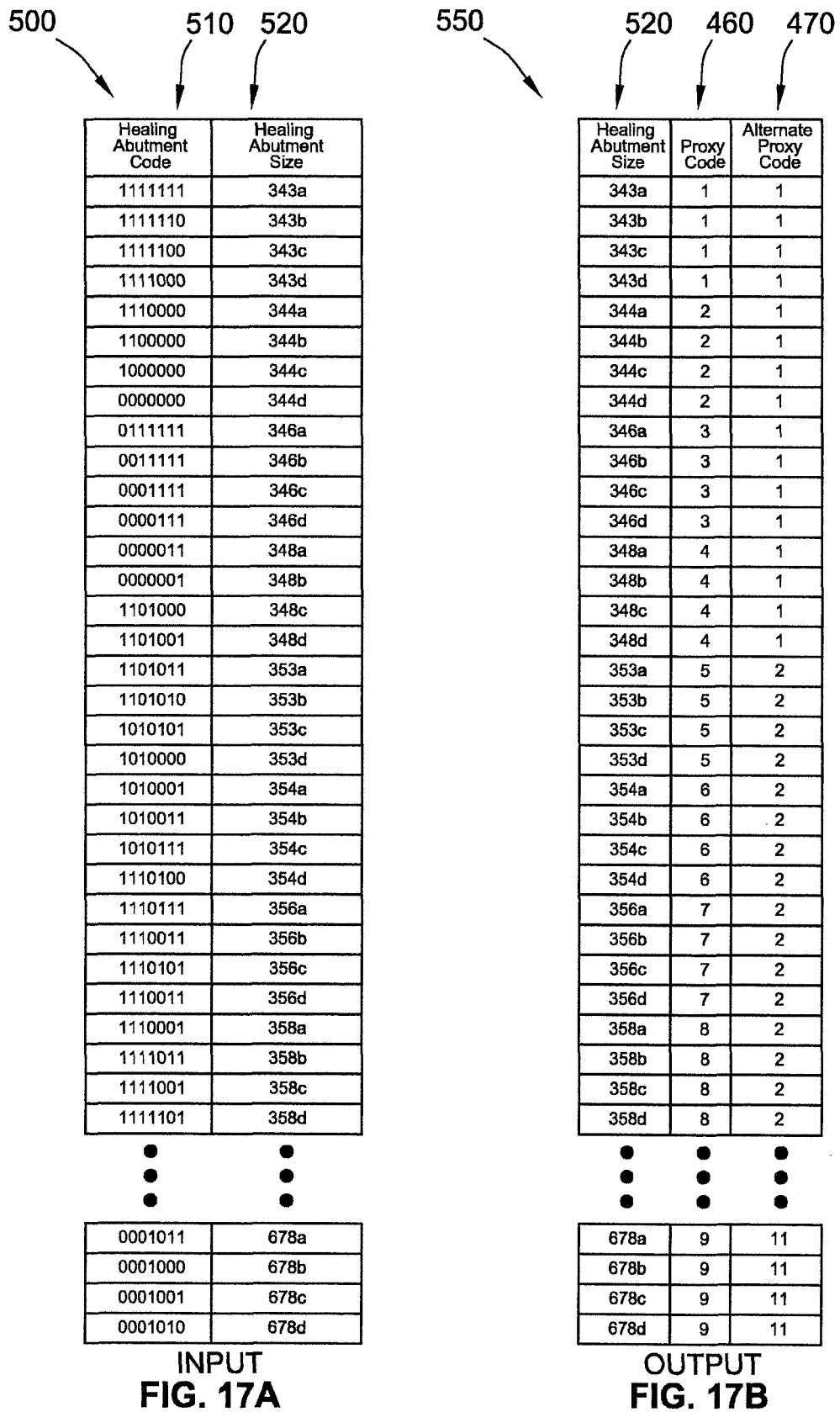
FIG. 17A is a second non-public code-to-abutment correlation library illustrating codes that correlate to specific sizes of healing abutments according to some implementations of the present disclosure.
FIG. 17B is a second non-public abutment-to-proxy correlation library illustrating virtual proxy abutments that correlate to the specific sizes of healing abutments of FIG. 17A.

The healing abutment 120 has a top surface 125 with informational markers 126 providing a code, which as described above, can be used to identify the healing abutment 120 with reference to a non-public code-to-abutment correlation library (e.g., non-public code-to-abutment correlation libraries 400 and 500 shown in FIGS. 16A and 17A, respectively). The scanning of the mouth 100 using the scanner 110 generates scan data that is used to create a virtual three-dimensional model 200 (FIG. 12) of the scanned portions of the mouth 100. The scan data and virtual three-dimensional model 200 is reproducible and transferable. In some instances, only the portion of the mouth 100 including the healing abutment 120 is scanned. In other instances, the entire mouth 100 is scanned.

Other methods of obtaining the virtual three-dimensional model 200 (FIG. 12) of the mouth 100 of the patient 101 are also possible. As shown in FIG. 11, a physical model 140 (e.g., a plaster or stone model) of at least a portion of the dental conditions in the mouth 100 of the patient 101 can be scanned using the scanner 110. The physical model 140 includes model teeth 142, model gingival tissue 144, and a model healing abutment 150. The model teeth 142 correspond with the actual teeth 102 in the mouth 100 of the patient 101. Similarly, the model gingival tissue 144 corresponds with the actual gingival tissue 104 in the mouth 100 of the patient 101. The model healing abutment 150 is an integral portion of the physical model 140. As such, an entire replica of the healing abutment 120 is not present in the physical model 140. Rather, the model healing abutment 150 only corresponds with the visible portion of the actual healing abutment 120 in the mouth 100 of the patient 101 (e.g., an anti-rotational feature of the healing abutment 120 is not represented in the physical model 140). The model healing abutment 150 has a top surface 155 with model informational markers 156 providing a code, which is used to identify the actual healing abutment 120 in the mouth 100 of the patient 101 with reference to a non-public code-to-abutment correlation library (e.g., non-public code-to-abutment correlation libraries 400 and 500 shown in FIGS. 16A and 17A, respectively). The top surface 155 of the portion of the model healing abutment 150 and the model informational markers 156 thereon correspond with the top surface 125 and the actual informational markers 126 of the actual healing abutment 120 in the mouth 100 of the patient 101. Specifically, the top surface 155 and the model informational markers 156 are substantially identical physical replicas of the top surface 125 and the actual informational markers 126. In addition to scanning a physical model 140, the scan data can be produced by scanning an impression (not shown) of the dental conditions of the mouth 100 that are used to create the physical model 140.

Thus, the virtual three-dimensional model can be created (i) by scanning a stone model (e.g., a replica of the patient's dental conditions including a replica of a portion of the healing abutment), (ii) by scanning impression material of an impression of the patient's dental conditions including the healing abutment, and/or (iii) by scanning the mouth of the patient directly including the healing abutment. Scanning can be accomplished using a laser scanning technique, a photographic scanning technique, or a mechanical sensing technique. These methods of scanning directly in a patient's mouth, an impression of the same, and a model of the same, using any of the aforementioned techniques, are described in further detail in U.S. Pat. No. 6,790,040, assigned to the assignee of the present disclosure, which was previously incorporated by reference herein in its entirety.

Figure 12:
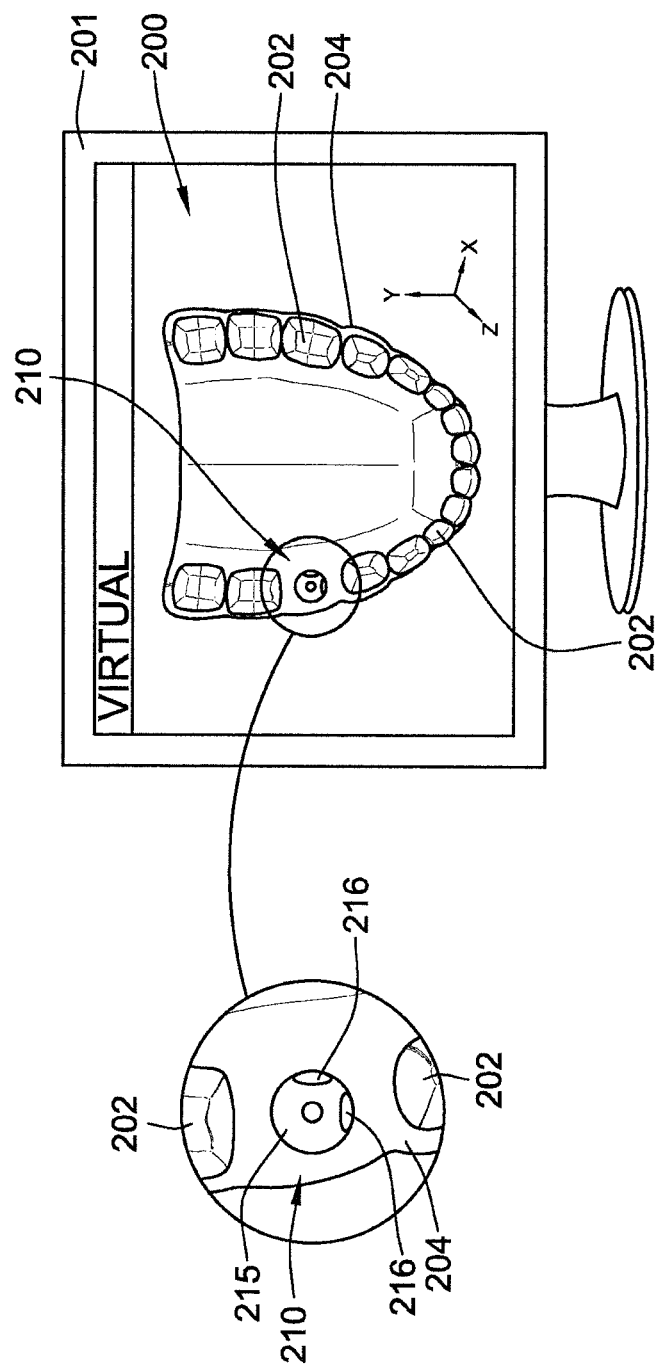
FIG. 12 illustrates a virtual three-dimensional model of a portion of a mouth of a patient developed from the scanning in FIG. 10 or FIG. 11.

Referring to FIG. 12, after the scanning of the mouth 100 is complete (e.g., the scan data is generated), the virtual three-dimensional model 200 is developed and can be viewed and/or manipulated (e.g., rotated in virtual space, translated in virtual space, modified, etc.) using, for example, a computer 201. The virtual three-dimensional model 200 is a virtual model of the scanned portion of the mouth 100 of the patient 101 and thus includes virtual teeth 202, virtual gingival tissue 204, and a virtual healing abutment 210, which correspond with the actual teeth 102, the actual gingival tissue 104, and the actual healing abutment 120, respectively in the mouth 100 of the patient 101. The virtual healing abutment 210 is an integral portion of the virtual three-dimensional model 200. As such, an entire virtual replica of the healing abutment 120 is not present in the virtual three-dimensional model 200. Rather, the virtual healing abutment 210 only corresponds with the visible portion of the actual healing abutment 120 in the mouth 100 of the patient 101 (e.g., an anti-rotational feature of the healing abutment 120 is not represented in the virtual three-dimensional model 200). The virtual healing abutment 210 has a top surface 215 with virtual informational markers 216 providing a code, which as described above, can be used to identify the actual healing abutment 120 in the mouth 100 of the patient 101 with reference to a non-public code-to-abutment correlation library (e.g., non-public code-to-abutment correlation libraries 400 and 500 shown in FIG. 16A or 17A, respectively). The top surface 215 of the virtual healing abutment 210 and the virtual informational markers 216 thereon correspond with the top surface 125 and the actual informational markers 126 of the actual healing abutment 120 in the mouth 100 of the patient 101. Specifically, the top surface 215 and the virtual informational markers 216 are substantially identical virtual replicas of the top surface 125 and the actual informational markers 126.

As described above, once the scanning is complete, the virtual three-dimensional model 200 is sent to a trusted third party (e.g., the manufacturer of the healing abutment 120) for identification of the healing abutment 120 and for creating a modified virtual three-dimensional model 200A (FIGS. 13 and 14) usable by a dental laboratory in designing and/or fabricating patient-specific components (e.g., a patient-specific prosthesis including a patient-specific abutment and/or a patient-specific crown) to be attached to the dental implant 111 installed in the mouth 100 of the patient 101.

To modify the virtual three-dimensional model 200 (FIG. 12) by removing the virtual healing abutment 210 (FIG. 12) and adding a virtual proxy abutment 220 (FIGS. 13 and 14), the code on the top surface 215 of the virtual healing abutment 210 (FIG. 12) is identified (e.g., determining the size and the orientation of the healing abutment 120) using software executing on, for example, the computer 201. The code can be identified automatically with or without input from a user. For example, in some implementations, a user of the computer 201 highlights the portion of the virtual three-dimensional model 200 including the top surface 215 (e.g., using the mouse of the computer 201 to encircle the top surface 215), which aids the computer 201 in accurately and/or efficiently (i) determining the location of the top surface 215 and (ii) identifying the code thereon (e.g., the code is identified as a 0-1-1-0 binary code).

After the code (e.g., 0-1-1-0) on the top surface 215 is identified, the computer 201, uses a library having information, which may be in the form of a look-up table (e.g., automatically and/or with input from a user of the computer 201) to obtain the identification of the healing abutment 120. Specifically, the computer compares the identified code (e.g., 0-1-1-0) with a list of possible codes in a non-public code-to-abutment correlation library (e.g., non-public code-to-abutment correlation library 400 shown in FIG. 16A). The comparison is used to identify the actual healing abutment 120 in the mouth 100 of the patient 101 that correlates with and/or corresponds to the code (e.g., 0-1-1-0) on the portion of the virtual healing abutment 210 in the virtual three-dimensional model 200. For purposes of the present example, the computer 201 may identify the code on the top surface 215 as a 0-1-1-0 code (e.g., the binary reading of the code starting at a certain location and moving clockwise around the top surface 215) and determine that the actual healing abutment 120 is a "343" healing abutment having a 3.4 mm platform diameter, a 3.8 mm maximum body diameter, and a 3.0 mm height.

Using the identified orientation and size of the actual healing abutment 120, the virtual three-dimensional model 200 can be modified to remove a portion thereof, thereby virtually exposing an underlying virtual implant 211 (FIG. 13) having an orientation (e.g., relative rotational position in space) and location (e.g., relative x-y-z position in space) corresponding to the orientation and location of the actual implant 111 in the mouth 100 of the patient 101. By "virtually exposing," it is not meant that removal of a portion of the virtual three-dimensional model 200 visually exposes the virtual implant on the computer 201 as no virtual implant is included in the scan data reproducible/viewable as the virtual three-dimensional model 200 (e.g., scanning the mouth 100 does not include scanning the implant 111, which is obscured). Rather, it is meant that the process of virtually removing the virtual healing abutment 210 can include virtually adding the virtual implant 211 or an upper portion thereof (FIGS. 13 and 14) into the virtual three-dimensional model 200 because the information from the healing abutment 210 is known. Additionally, using the identified orientation and size of the actual healing abutment 120, the modification of the virtual three-dimensional model 200 can further include modifying the virtual three-dimensional model 200 to include a virtual gingival aperture leading to the virtual implant, where the virtual gingival aperture includes virtual gingival contours that are inferred from the outer contours of the identified actual healing abutment 120. The virtual gingival aperture can be visible in the model or fully or partially hidden (e.g., by a virtual proxy abutment as discussed below). The following process can be used to expose the implant 111 within the virtual model 200 and/or to add the virtual gingival aperture to the model 200.

A portion of the virtual three-dimensional model 200 can be removed corresponding to a complete virtual healing abutment because the size of the actual healing abutment 120 in the mouth 100 of the patient 101 is known. That is, once the actual healing abutment 120 is identified as a "343" healing abutment, a virtual "343" healing abutment (e.g., from a library of known virtual healing abutments) can be imported from a memory device (e.g., a storage medium) into the software that displays the virtual three-dimensional model 200 on the computer 201. After importing the virtual "343" healing abutment (not shown), the virtual "343" healing abutment is matched to and aligned with the portion of the virtual healing abutment 210 in the virtual three-dimensional model 200. Specifically, the outer contours of the virtual "343" healing abutment are matched to the outer contours of the virtual healing abutment 210 in the virtual three-dimensional model 200. Such a process is known as "snapping" the imported virtual "343" healing abutment to the virtual healing abutment 210 in the virtual three-dimensional model 200.

After the snapping, using a Boolean subtraction process, the virtual three-dimensional model 200 can be modified to remove a three-dimensional portion of the virtual three-dimensional model 200 corresponding to the complete virtual "343" healing abutment (e.g., not just the visible portion of the virtual healing abutment 210). Because the orientation and location of a corresponding virtual non-rotational feature 218 and a virtual table 219 of a virtual implant 211 is known because of the information from the "343" healing abutment, the implant's upper portion is also known. The upper portion of the virtual implant 211 is the important part, because it includes the geometric information to which the prosthetic components will be attached. The virtual implant 211 includes the virtual male anti-rotational feature 218, which has an orientation corresponding to the orientation of the female anti-rotational feature of the virtual "343" healing abutment (e.g., which also corresponds with the orientation of the actual female anti-rotational feature of the actual healing abutment 120). Further, the virtual implant 211 includes the table 219, which has a location corresponding to the location of a seating surface (e.g., implant vertical mating surface) of the virtual "343" healing abutment.

In some implementations, after the snapping and prior to the Boolean subtraction process, the virtual implant 211 (shown in FIG. 13), corresponding to the actual implant 111 in the mouth 100 of the patient 101 (e.g., the virtual implant 211 is substantially an exact virtual replica of the implant 111), is imported into the software package used to display the virtual three-dimensional model 200 on the computer 201. The virtual implant 211 is then virtually mated with the virtual 343 healing abutment (not shown) using the software package on the computer 201, and as such, the virtual implant 211 is automatically positioned within the virtual three-dimensional model 200 with an orientation and location corresponding to the orientation and position of the actual implant 111 in the mouth 100 of the patient 101. In such implementations, the virtual "343" healing abutment is then subtracted or removed from the virtual three-dimensional model 200, thereby exposing an upper portion of the virtual implant 211 as shown in FIG. 13.

To avoid the private information regarding the details of the actual healing abutments becoming public via the virtual healing abutment 210 within the virtual three-dimensional model 200, the virtual three-dimensional model 200 is modified to include a virtual proxy abutment 220 or a portion of a virtual proxy abutment (e.g., an upper or supragingival portion of a virtual proxy abutment including a proxy code thereon, a narrow virtual proxy abutment 820 shown in FIGS. 21A and 21B, a floating virtual proxy abutment 920 shown in FIGS. 22A and 22B, etc.) in place of the virtual healing abutment 210 (e.g., by use of the non-public abutment-to-proxy correlation libraries 450, 550 in FIGS. 16B and 17B) and becomes a modified virtual three-dimensional model 200A. The modified virtual three-dimensional model 200A may be sent to a third party for use in designing and fabricating the patient-specific components with the virtual proxy abutment 220 (or the portion of the virtual proxy abutment) within the modified virtual three-dimensional model 200A. As described below, the virtual proxy abutment 220 has physical characteristics (e.g., proxy code) that are publicly known through a publicly available proxy abutment library that can be accessed by the third party.

The virtual proxy abutment 220 is selected based on the healing abutment 120 that has been identified through the use of the non-public abutment-to-proxy correlation library 450 or 550 (FIGS. 16B and 17B). Continuing with the above exemplary implementation where the healing abutment 120 was identified as a "343" healing abutment, that determined size of the healing abutment is used with a non-public abutment-to-proxy correlation library 450 (FIG. 16B) to choose a proxy abutment. The abutment-to-proxy correlation library 450 is used to convert a particular healing abutment (e.g., 343 healing abutment) to a proxy abutment. As an example, in FIG. 16B, the identified the "343" healing abutment correlates with proxy code of 1 (column 460), which corresponds to a known virtual proxy abutment 220 (FIGS. 13-14).

In FIG. 14, the selected virtual proxy abutment 220 includes virtual proxy informational markers 226, which define a code corresponding with the proxy code of 1. As such, a dental laboratory having/viewing the modified virtual three-dimensional model 200A (FIG. 14) including the virtual proxy abutment 220 can read the proxy code of 1 and reference a publicly available proxy abutment library 355 (FIG. 15) to determine the size and orientation of the virtual proxy abutment 220, which is used in designing and fabricating patient-specific components to be attached to the implant 111. Specifically, for example, in the implementations where only an upper or supragingival portion of the virtual proxy abutment 220 is included in the modified virtual three-dimensional model 200A, the dental laboratory having the modified virtual three-dimensional model 200A uses its design software in a similar fashion as to how the virtual healing abutment 210 was identified and removed from the virtual three-dimensional model 200. That is, the dental laboratory first identifies the proxy code by analyzing the virtual proxy informational markers 226 on the top surface of the virtual proxy abutment 220. Then the dental laboratory, using for example a computer executing design software, imports a complete virtual proxy abutment (e.g., a complete CAD replica of the virtual proxy abutment having the identified proxy code stored, for example, in the proxy abutment library 355) into the modified virtual three-dimensional model 200A and snaps the imported virtual proxy abutment to the portion of the virtual proxy abutment 220 in the modified virtual three-dimensional model 200A. Then the virtual proxy abutment 220 can be removed, thereby virtually exposing a virtual implant and/or a virtual gingival aperture leading to the virtual implant to be used in completing the designing of the patient-specific prosthesis.

Alternatively to the modified virtual three-dimensional model 200A only including a portion of the virtual proxy abutment 220, the modified virtual three-dimensional model 200A can include a complete virtual proxy abutment (e.g., a complete CAD replica of the virtual proxy abutment having the identified proxy code stored, for example, in the proxy abutment library 355). As shown in FIG. 13, the complete virtual proxy abutment 220 includes a female anti-rotational feature 228 and a seating surface 229. Proper virtual placement of the virtual proxy abutment 220 on the virtual implant 211 requires that (i) the female anti-rotational feature 228 mates correspondingly with the male anti-rotational feature 218 of the virtual implant 211 and (ii) the seating surface 229 abuts the table 219 of the virtual implant 211. Such a proper mating is shown in FIG. 14, where the virtual proxy abutment 220 is mated with the virtual implant 211 in the modified virtual three-dimensional model 200A.

While the modified virtual three-dimensional model 200A is shown as including the virtual implant 211 therein, the modified virtual three-dimensional model 200A does not need to include the virtual implant 211. Rather, the virtual three-dimensional model 200 can be modified such that the modified virtual three-dimensional model 200A only adds the complete virtual proxy abutment 220 or the portion of the virtual proxy abutment 220. In such implementations, the virtual implant 211 is not needed to determine the orientation and location for the virtual proxy abutment 220 because the virtual proxy abutment 220 is located and oriented in the modified virtual three-dimensional model 200A the same way as the virtual healing abutment 210, which is located and oriented in the same way as the patient's actual healing abutment to which the actual implant is attached. Hence, knowing the location and orientation of the lower seating surface 229 and anti-rotational feature 228 of the virtual proxy abutment 220 means that the location and orientation of the corresponding mating surface and anti-rotational feature of the actual implant 111 are known. Thus, as understood by the skill artisan, the modified virtual three-dimensional model 200A (with or without the virtual implant 211) including the orientation and location of the female anti-rotational feature 228 and the seating surface 229 of the virtual proxy abutment 220 is sufficient for a third party (e.g., a dental laboratory) to create patient-specific components for attachment to the implant 111 in the mouth 100 of the patient 101 such that those patient-specific components can be attached to the implant 111 with the proper location and orientation and provide an aesthetically pleasing dental prosthesis.

In summary, the modified virtual three-dimensional model 200A just needs to include some information (e.g., a complete CAD virtual proxy abutment including the female anti-rotational feature 228 and the seating surface 229, a portion of a virtual proxy abutment including the proxy code, a virtual implant including a non-rotational feature and platform, a virtual proxy abutment attached to a virtual implant, a narrow virtual proxy abutment including a proxy code, a floating virtual proxy abutment including a proxy code, etc.) from which the location and orientation of the implant in the mouth of the patient can be determined and from which a gingival aperture (e.g., a predicted or inferred gingival aperture based on the contours of the actual healing abutment and/or the proxy abutment) can be determined. That is, the dental laboratory that receives the modified virtual three-dimensional model 200A, can develop the patient-specific prosthesis (e.g., patient-specific abutment, patient-specific crown, etc.) so long as the design software being used by the dental laboratory is given and/or can determine (1) the location and orientation of a virtual implant that corresponds with the location and orientation of the actual implant in the mouth of the patient and (2) the virtual gingival aperture leading to the virtual implant that corresponds with the actual gingival aperture (e.g., predicted actual gingival aperture) in the mouth of the patient. Even further, in some implementations, only a coordinate system of the location of the platform of the implant and orientation of the non-rotational feature of the implant is needed. That is, the virtual implant itself does not need to be depicted in the modified virtual three-dimensional model 200A, just a starting location and orientation for the patient-specific prosthesis is needed.

Figure 15:
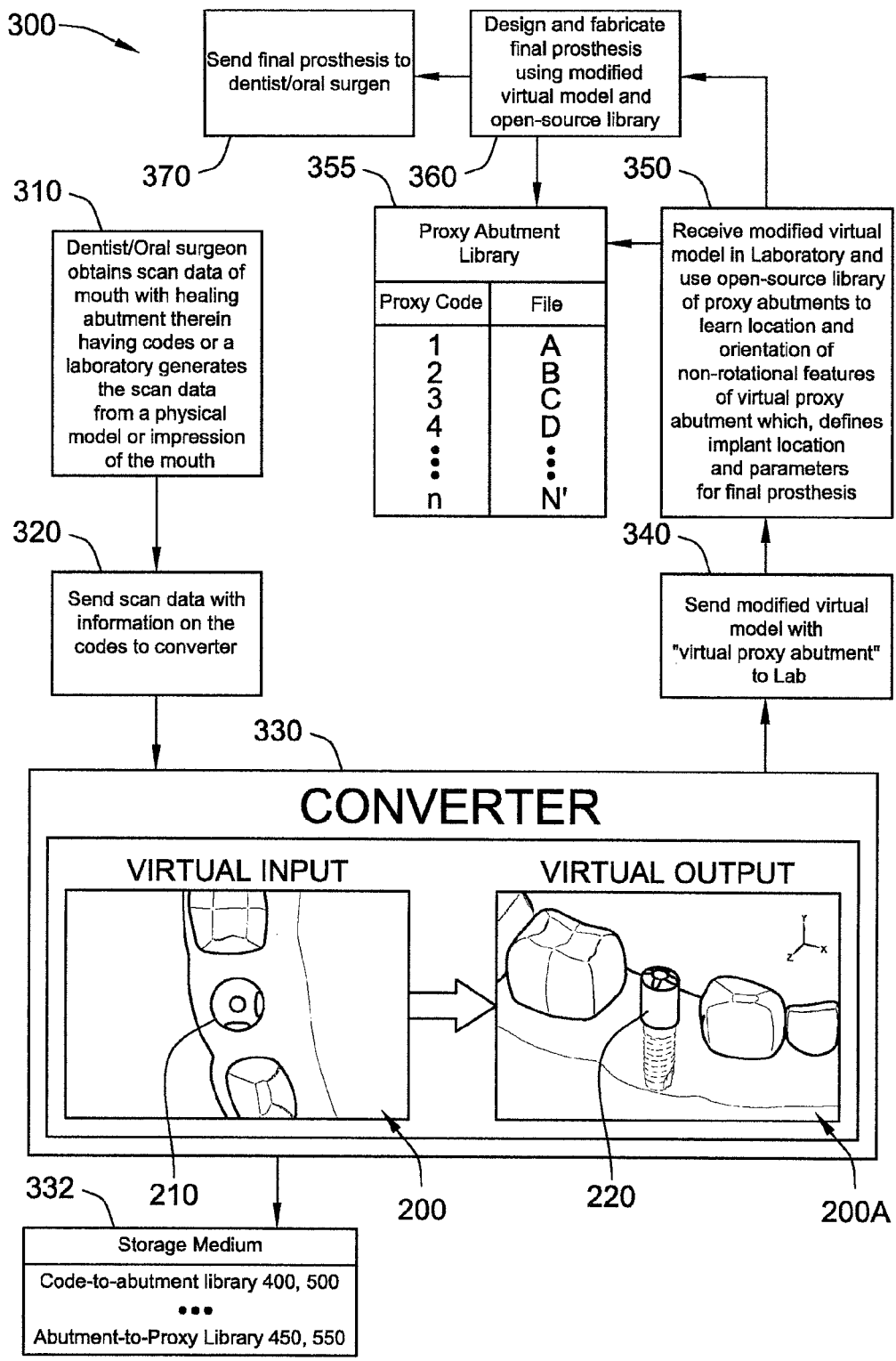
FIG. 15 is a flow chart of a method for making a patient-specific prosthesis using the process according to the present disclosure.

FIG. 15 describes a general summary of converting a virtual three-dimensional model 200 having a virtual healing abutment 210 into a modified virtual three-dimensional model 200A including a virtual proxy abutment 220. The process 300 begins with obtaining scan data of a patient's mouth having a healing abutment with a code thereon (step 310). The scan data can be obtained by, for example, a dentist, an oral surgeon, a dental assistant, a clinician, a dental lab (from a stone model and/or an impression), etc. The scan data is reproducible as a virtual three-dimensional model of at least a portion of the patient's mouth and includes therein a virtual healing abutment having the code. After the scan is complete, the scan data is sent to a trusted party who has access to the non-public code-to-abutment correlation library (e.g., the manufacturer of the healing abutment in the mouth of the patient or a licensed affiliate) (step 320). The received scan data is input into a converter 330 that may include one or more computers executing one or more software packages, which converts the inputted virtual three-dimensional model 200 including the virtual healing abutment 210 into the modified virtual three-dimensional model 200A including the virtual proxy abutment 220. The converter 330 (and processors associated therewith) access a storage medium 332 that includes the non-public code-to-abutment correlation library 400 and/or 500 (FIGS. 16A and 17A) and a non-public abutment-to-proxy correlation library 450 and/or 550 (FIGS. 16B and 17B). After the conversion, the modified virtual three-dimensional model 200A is sent to a dental laboratory (step 340). Once received, the dental laboratory uses a publicly known or open-source proxy-abutment library 355 to identify the virtual proxy abutment 220 in the modified virtual three-dimensional model 200A (step 350). The publicly known or open-source proxy-abutment library 355 includes an electronic file (e.g., file A, B, C, D . . . N') that defines the dimensions of each type of proxy abutment (e.g., code 1, 2, 3, 4 . . . n). Thus, all information (e.g., exterior contours) about each proxy abutment is publicly available. Thus, step 350 includes identifying the size and orientation information of the virtual proxy abutment 220. The dental laboratory then creates patient-specific components (e.g., abutments, prosthesis) to fit on the actual implant in the mouth of the patient who has the healing abutment corresponding to the virtual healing abutment 210 (step 360). After the patient-specific components are created, they are sent to, for example, the dentist for installation in the mouth of the patient after removal of the healing abutment (step 370).

While the above disclosure describes a modified virtual three-dimensional model 200A (FIG. 14) being sent to a third party for use in designing and creating patient-specific components, in some implementations, an actual physical model (not shown) of some or all of the modified virtual three-dimensional model 200A is created and sent to the third party along with the modified virtual three-dimensional model 200A. Such an actual physical model (not shown) can be created using a rapid prototype machine and/or a three-dimensional printer coupled to, for example, the computer 201. The actual physical model can include an implant analog portion (e.g., an integral implant analog portion made of the same material as the rest of the rapid-prototyped actual physical model or an implant analog placed in a receptacle of the rapid-prototyped actual physical model) and be used to try-in the custom components. For example, if only a custom abutment is created from the modified virtual three-dimensional model 200A, then the actual physical model may be useful for helping to create and fit a tooth-colored prosthesis (e.g., a crown) on the custom abutment.

Examples of the various non-public code-to-abutment correlation libraries and non-public abutment-to-proxy correlation libraries that can be stored by the storage medium 332 and used by the converter 330 in FIG. 15 will now be described. Referring initially FIG. 16A, an exemplary non-public code-to-abutment correlation library 400 includes a healing abutment code column 410 and a healing abutment size column 420. The non-public code-to-abutment correlation library 400 can be printed and used by a person to identify healing abutments. Or, the non-public code-to-abutment correlation library 400 is stored in a memory device (e.g., storage medium 332 in FIG. 15) associated with the computer 201 (FIGS. 12-14) that can be accessed to determine the particular healing abutment that corresponds to the code that is present in the virtual three-dimensional model 200. The code-to-abutment correlation library 400 is on the "INPUT" side of the converter 330 (FIG. 15) in that the three-dimensional virtual model 200 inputted into the converter 330 and the code-to-abutment correlation library 400 determines the healing abutment used on the patient based on the code within the virtual three-dimensional model 200.

The healing abutment code column 410 includes, in this case, a list of binary codes. For example, the list of binary codes can include every binary code used on a particular set of healing abutments sold by a manufacturer (e.g., for a given year). The binary codes with one healing abutment set can have the same number of digits or a different number of digits (e.g., 4 digit codes, 5 digit codes, 10 digit codes, etc., or any combination thereof). For example, if thirty-two or less healing abutments are present in one set, a five-digit binary code can define each member of the set.

The healing abutment size column 420 includes a list of different healing abutments using a shorthand representation. The shorthand representation includes three digits XYZ, where X represents the platform diameter of the healing abutment, Y represents the maximum body diameter of the healing abutment, and Z represents the height of the healing abutment. For example, the first shorthand number (XYZ) in the healing abutment size column 420 is "343," which is a shorthand representation of the healing abutment having a 3.4 mm platform diameter, a 3.8 mm maximum body diameter, and a 3.0 mm height.

The list of sizes (XYZ) can include every sized healing abutment sold by a manufacturer (e.g., for a given year). The sizes in the non-public code-to-abutment correlation library 400 can be organized in any manner or randomly. As shown in the healing abutment size column 420, the sizes are organized in an ascending order starting with the healing abutments having the smallest platform diameter. Further, for each platform diameter and maximum body diameter combination (e.g., 34Z, 45Z, 67Z, where "Z" represents the height), the healing abutments are then organized in ascending height. For example, the third group of healing abutments is the "44Z" group, which includes the 443, 444, 446, and 448 healing abutments (where Z represents the height). Each healing abutment in the 44Z group has the same platform diameter and maximum body diameter; only the height differs. For example, the 443 healing abutment has a 3 mm height and the 448 healing abutment has an 8 mm height. As another example, the fifth group of healing abutments is the "46Z" group, which includes the 463, 464, 466, and 468 healing abutments, where the 464 healing abutment has a 4 mm height and the 466 healing abutment has a 6 mm height.

As is evident from FIG. 16A, the binary codes each have a one-to-one relationship with the different sized healing abutments. For example, binary code 0-1-1-0-1-0 correlates only with a 343 healing abutment and the 343 healing abutment only correlates with binary code 0-1-1-0-1-0. For another example, binary code 0-1-1-1-1-1 correlates only with a 668 healing abutment and the 668 healing abutment only correlates with binary code 0-1-1-1-1-1. However, as will be described with reference to FIGS. 17A-17B, in some implementations of the present disclosure, a one-to-one relationship is not needed such that a 343 healing abutment can be associated with multiple codes.

FIG. 16B illustrates an example of a non-public proxy-to-abutment correlation library 450 that may be used by the converter 330 (FIG. 15) to create the OUTPUT from the converter 330. Specifically, after a particular healing abutment has been identified through the use of the non-public code-to-abutment correlation library 400, a virtual proxy abutment is used to replace the virtual healing abutment within the virtual three-dimensional model 200. The proxy-to-abutment correlation library 450 includes the healing abutment size column 420, a proxy code column 460, and an alternative proxy code column 470. The system may use only the proxy code column 460 or the alternative proxy code column 470. Each code within those columns corresponds to a particular proxy abutment. Accordingly, there are forty-four different proxy abutments that are needed if the system uses the proxy code arrangement according to column 460. For each particular healing abutment, the converter would replace the virtual healing abutment with a corresponding virtual proxy abutment.

Alternatively, if the proxy code arrangement according to column 470 (FIG. 16B) is used, there are only eleven different proxy abutments that are needed. In the example shown, the first four healing abutments, which are 343, 344, 346, 348, only differ from each other by their heights of 3 mm, 4 mm, 6 mm, and 8 mm. Accordingly, the same proxy abutment (code 1) could be used for all four of these healing abutments, as such a proxy abutment (code 1) would have the same platform diameter and the same maximum body diameter as those four healing abutments (343, 344, 346, 348), but would have a different height. However, the height of the proxy abutment is somewhat irrelevant in that only the location and orientation of the proxy abutment's anti-rotational feature and lowermost seating surface are needed to build a prosthesis that will be accurately placed on the patient's implant. The proxy abutment may have a code on its upper surface to identify it within the publicly available proxy abutment library 355. Or, some other identification information can be included within the modified virtual three-virtual three-dimensional model 200A to advise the receiving third-party which proxy abutment has been used within the modified virtual three-virtual three-dimensional model 200A.

In the alternate proxy code column 470 of the abutment-to-proxy correlation library 450 of FIG. 16B, each of the eleven proxy codes corresponds to a grouping of four healing abutments in which the only difference within the grouping is the healing abutment height. Accordingly, the alternate proxy code 470 provides a way of reducing the number of publicly available proxy abutments and publicly available proxy codes that are used to create the final prosthesis.

FIG. 17A illustrates another exemplary non-public code-to-abutment correlation library 500 that includes a healing abutment column 510 and a healing abutment size column 520. While the non-public code-to-abutment correlation library 500 is similar to the non-public code-to-abutment correlation library 400 in FIG. 16A in many respects, the non-public code-to-abutment correlation library 500 does not have a one-to-one correlation between codes and each healing abutment. Rather, the non-public code-to-abutment correlation library 500 has a four-to-one relationship. For example, binary codes 1-1-1-1-1-1, 1-1-1-1-1-0, 1-1-1-1-1-0-0, and 1-1-1-1-0-0-0 each correlate with a 343 healing abutment having a 3.4 mm platform diameter, a 3.8 mm maximum body diameter, and a 3 mm height. The only difference between the four 343 healing abutments represented as 343a, 343b, 343c, and 343d in column 520 (FIG. 17A) is the code on the respective top surfaces. For another example, binary codes 0-0-0-1-0-1-1, 0-0-0-1-0-0-0, 0-0-0-1-0-0-1, and 0-0-0-1-0-1-0 each correlate with a 678 healing abutment having a 6 mm platform profile diameter, a 7.5 mm maximum body diameter, and an 8 mm height. Again, the only difference between the four healing abutments represented as 678a, 678b, 678c, and 678d in column 520 is the code on the respective top surfaces. From a functional perspective, there is no real difference in the manner in which each of these four healing abutments will function while in the patient's mouth because the codes are only for identifying a particular healing abutment. Consequently, healing abutments 678a, 678b, 678c, and 678d are actually the same healing abutment.

FIG. 17B illustrates another exemplary non-public proxy-to-abutment correlation library 550 that may be used by the converter 330 (FIG. 15) to create the OUTPUT from the converter 330. While the non-public proxy-to-abutment correlation library 550 is similar to the non-public proxy-to-abutment correlation library 450 in FIG. 16B in many respects, the non-public proxy-to-abutment correlation library 550 does not have a one-to-one correlation between proxy codes and each healing abutment. Rather, the non-public proxy-to-abutment correlation library 550 has a four-to-one relationship. For example, healing abutments 343a, 343b, 343c, and 343d (each having a 3.4 mm platform diameter, a 3.8 mm maximum body diameter, and a 3 mm height) each correlate with a proxy abutment having a proxy code of 1. The only difference between the four 343 healing abutments represented as 343a, 343b, 343c, and 343d in column 520 (FIG. 17B) is the code on the respective top surfaces.

Alternatively, if the proxy code arrangement according to column 470 (FIG. 17B) is used, there are only eleven different proxy abutments that are needed. In the example shown, the first sixteen healing abutments, which are 343a, 343b, 343c, 343d, 344a, 344b, 344c, 344d, 346a, 346b, 346c, 346d, 348a, 348b, 348c, and 348d, only differ from each other by their heights of 3 mm, 4 mm, 6 mm, and 8 mm. Accordingly, the same proxy abutment (code 1) could be used for all sixteen of these healing abutments, as such a proxy abutment (code 1) would have the same platform diameter and the same maximum body diameter as those sixteen healing abutments (343a, 343b, 343c, 343d, 344a, 344b, 344c, 344d, 346a, 346b, 346c, 346d, 348a, 348b, 348c, and 348d), but would have a different height.

As described above, to make it difficult for unscrupulous third parties to correlate the codes on the healing abutments with a particular size of healing abutment and/or to correlate the proxy codes on the proxy abutments with a particular size of healing abutment, a rolling-code system for the codes and/or for the proxy codes can be implemented by the manufacturer of the healing abutments. For example, the codes on the different sizes of healing abutments can be changed randomly and/or changed at specific times. For example, every six months or every twelve months, etc., the code or codes used for identifying the 343 healing abutment can be changed, and such a change would only be known to the keeper (e.g., the manufacturer) of the non-public code-to-abutment correlation library. For another example, the proxy codes on the proxy abutments can be changed randomly and/or changed at specific times. Further, the codes (e.g., the codes on the healing abutments and/or the proxy codes on the proxy abutments) can be changed to look like completely new codes never before used and/or seen (e.g., adding a new notch or a new informational marker in a new location on the top surface of all healing abutments). Alternatively or additionally, one or more of the codes for one or more of the healing abutments can be changed to use a code previously used to identify a differently sized healing abutment. For example, during a first period of time as shown in FIG. 16A, the 343 healing abutment is associated with a first code of 0-1-1-0-1-0 and the 678 healing abutment is associated with a second code of 1-0-1-1-1-1. The manufacturer can then switch the codes for the various healing abutments for a second period of time where, for example, the 343 healing abutment is not associated with the first code of 0-1-1-0-1-0, but rather the 343 healing abutment is now (e.g., for the second period of time) associated with the second code of 1-0-1-1-1-1. Similarly, the 678 healing abutment can be switched to be associated with the first code of 0-1-1-0-1-0 during the second period of time. Such a rolling-code system aids in preventing unscrupulous third parties from trying to reverse engineer the non-public libraries of the present disclosure.

Further, as discussed above, the present disclosure maintains one or more libraries in secrecy. For example, the non-public code-to-abutment correlation library 400 and the non-public abutment-to-proxy correlation library 450 are described as being maintained in secrecy by the manufacturer of the healing abutments with the codes thereon (exception for trusted third parties/affiliates). It was also discussed above that the codes on the healing abutments can be changed from time-to-time (e.g., a rolling-code system). Many advantages are derived for the manufacturer by maintaining these and similar libraries in secrecy and by changing the codes from time-to-time. For example, maintaining the libraries in secrecy and/or changing the codes from time-to-time, aids in preventing unscrupulous third parties form attempting to copy and/or reproduce (e.g., reverse engineer) the non-public libraries. As such, users of the healing abutments of the present disclosure are encouraged to return to the manufacturer and/or trusted third parties for additional purchases (e.g., a third party sends a virtual three-dimensional model to be decoded for a fee). Further, as the manufacturer controls the codes and when they are changed, it is easy for the manufacturer to also maintain a publicly available proxy abutment library for use by the manufacturer's customers. Further, by reducing the possibility that an unscrupulous third party knocks-off the non-public libraries, the manufacturer is able to provide its services at more economical price.

Further, as described above, the present disclosure provides for modified virtual three-dimensional models including a proxy abutment having a publicly available proxy code. Such a modified virtual three-dimensional model can be referred to as a scan-body-level model. These modified virtual three-dimensional models of the present disclosure can be derived from and/or create based on scan data from virtually any scanner so long as the scanner produces an open architecture file format (e.g., a non-proprietary file format such as an open STL file). Further, the modified virtual three-dimensional models can readily be sent to multiple dental laboratories using virtually any dental design software that they prefer so long as the dental design software accepts the open architecture file format. As such, the flexibility of the coded healing abutments of the present disclosure is greatly increased as virtually all open architecture scanners and design software can be used with the disclosed coded healing abutments. Further, use of the proxy abutments allows for the wide spread use of the coded healing abutments of the present disclosure without having to make the decryption keys (e.g., the code-to-abutment library) for the codes public.

In summary, the present disclosure provides a system that is cost effective and simple to maintain and use as customers only need knowledge of a single publicly available proxy abutment library and can use a wide variety of scanners and design software.

Figure 18:
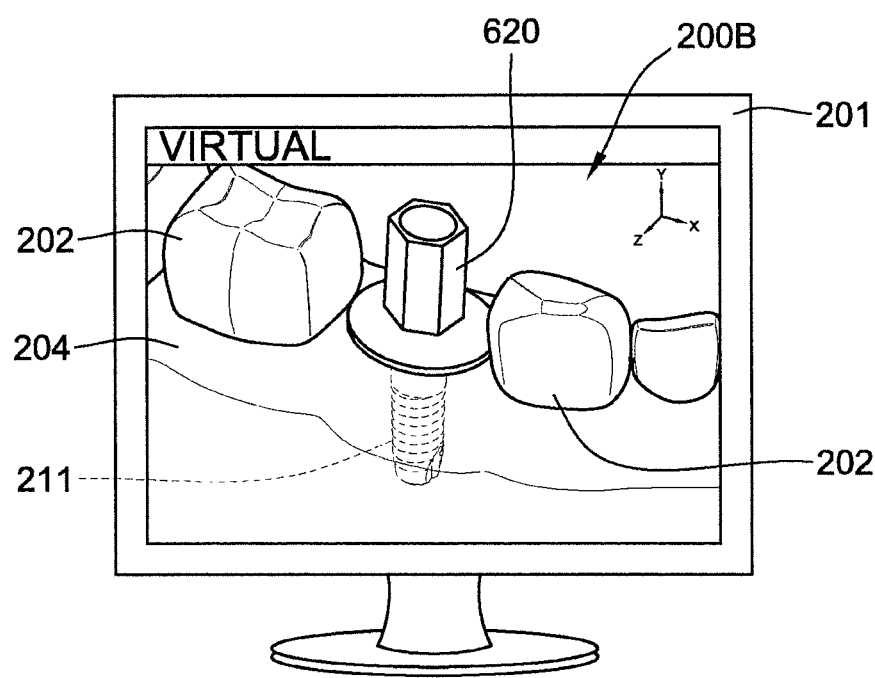
FIG. 18 illustrates an alternative implementation in which the modified virtual three-dimensional model of the mouth of the patient includes a virtual insert abutment attached to a virtual implant, as opposed to a virtual proxy abutment.

Referring to FIG. 18, while the above disclosure discusses a modified virtual three-dimensional model 200A including a proxy abutment 220 (FIGS. 13 and 14), in lieu of using the modified virtual three-dimensional model 200A, an alternative modified virtual three-dimensional model 200B including a virtual link abutment 620 can be used to design patient-specific components. The modified virtual three-dimensional model 200B is similar to the modified virtual three-dimensional model 200A in many respects; however, instead of including the virtual proxy abutment 220, the modified virtual three-dimensional model 200B includes a virtual link abutment 620. The modified virtual three-dimensional model 200B is referred to as an abutment-level design (as opposed to an implant level design). The virtual link abutment 620 is a standardized abutment and/or insert that is virtually placed on the underlying virtual implant 211 and a custom prosthesis is designed thereon. The virtual link abutment corresponds to an actual link abutment (not shown) that can be physically coupled with the implant 111 in the mouth of the patient as a portion of the final patient-specific prosthesis (e.g., a patient-specific abutment is directly attached to the link abutment that is directly attached to the implant). Thus, the laboratory designing the patient-specific components can design and add the prosthetic components (e.g., patient-specific abutment and/or crown) on top of the virtual link abutment 620 and then fabricate the same. In summary, the link abutment is a standard abutment known to everyone and attaches to the actual implant. As such, the laboratory can build the final components on the virtual link abutment 620 in the modified virtual three-dimensional model 200B.

Figure 19:
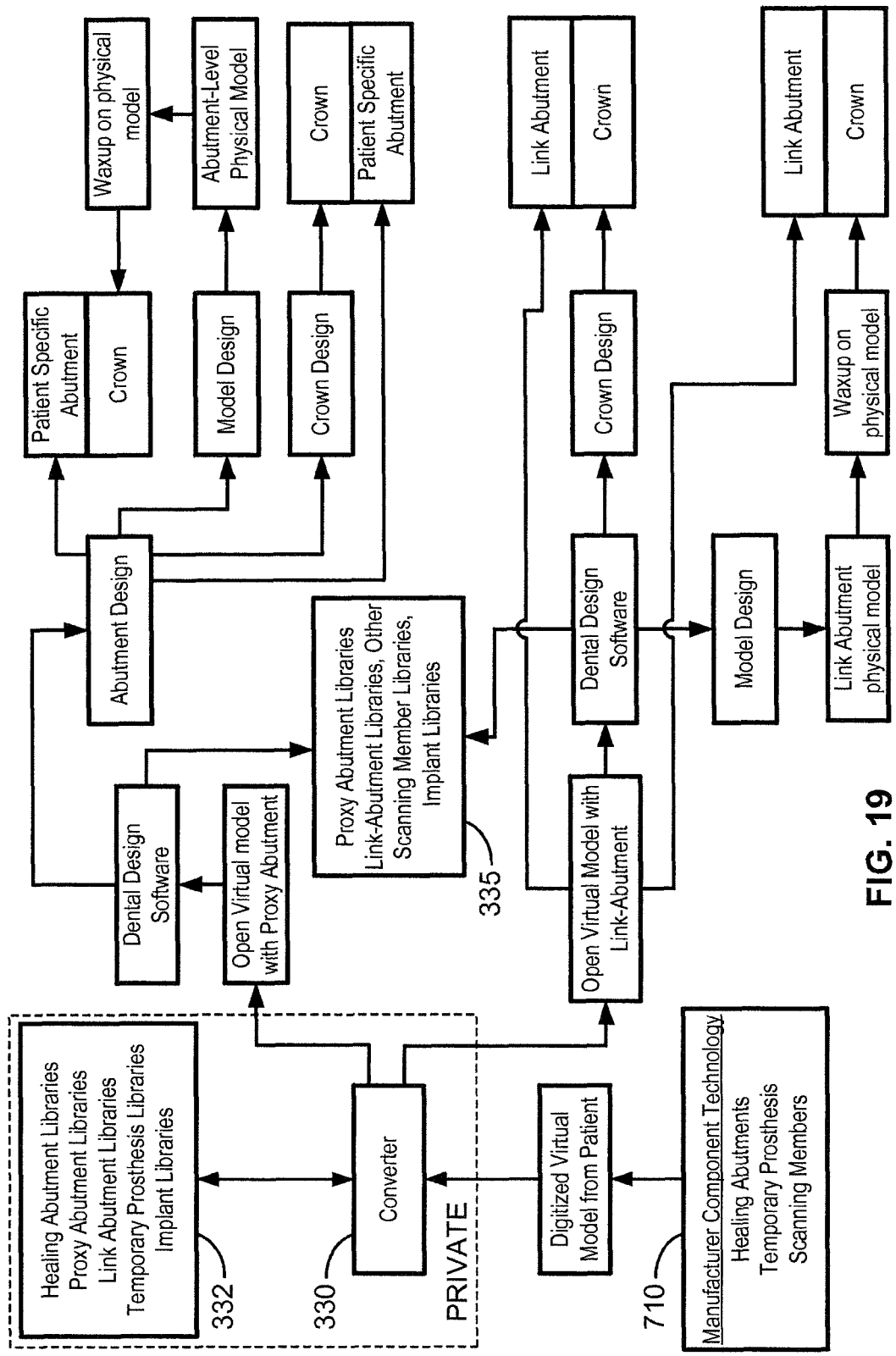
FIG. 19 is a flow chart showing the overall process for making a patient-specific prosthesis using the process of the present disclosure.

Referring to FIG. 19, FIG. 19 is similar to FIG. 15 except that it provides some additional details regarding the products that are delivered to the third parties pursuant to the present disclosure. The manufacturer of a dental-implant technology provides various components 710 that are scannable, preferably with codes thereon, by its customers or third parties affiliated with its customers. When one of these components (e.g., the healing abutment 120 of FIG. 10) is scanned in association with a particular patient to form a virtual three-dimensional model (e.g., virtual three-dimensional model 200A of FIG. 12), the virtual three-dimensional model is received by the converter 330 within a private environment associated with the dental manufacturer or a trusted third party. The converter 330 accesses the storage medium 332 within this private environment. The storage medium 332 contains electronic-file libraries associated with the various components 710. The electronic files include the specific codes that are located on the components 710 that help to identify each particular component and distinguish it from another similar component. As described above, the converter 330 then develops the modified virtual three-dimensional model 200A (FIG. 14) that includes the virtual proxy abutment 220 (FIGS. 13 and 14) or the modified virtual three-dimensional model 200B (FIG. 18) that includes the link abutment 620.

When the modified virtual three-dimensional model 200A includes the virtual proxy abutment 220 (FIGS. 13 and 14), the dental design software (or a user thereof) accesses the publicly available library 355 with information about the virtual proxy abutments and uses that information to design a patient-specific prosthesis. The patient-specific prosthesis, which is manufactured after it has been designed, can be accompanied by other deliverable products in accordance with at least two alternatives.

In a first alternative, an abutment-level physical model of the mouth of the patient can be designed and manufactured, for example via rapid-prototyping techniques as disclosed in U.S. Pat. No. 8,185,224, which is commonly owned by the assignee of the present disclosure and is hereby incorporated by reference herein in its entirety. According to some such implementations, the abutment-level physical model includes an integral abutment structure made of the same material as the rest of the rapid-prototyped physical model. According to some other implementations, the abutment-level physical model includes an abutment analog structure and/or an abutment analog attached to an implant analog which is coupled to the rest of the physical model (the rest of the physical model can be rapid prototyped and/or a stone model). In some implementations, the abutment analog, in the abutment-level physical model, is a patient-specific abutment that is a component of a final prosthesis (e.g., a patient-specific prosthesis) to be attached to the implant in the mouth of the patient. In some other implementations, the abutment analog, in the abutment-level physical model, is a standard abutment or insert (e.g., a link abutment insert) that is a component of a final prosthesis (e.g., a patient-specific prosthesis) to be attached to the implant in the mouth of the patient. Once the abutment-level physical model is completed (by one of the above techniques or by another technique), the abutment-level physical model is then delivered to a laboratory. The laboratory can then perform standard wax-up techniques on the abutment-level physical model to develop a prosthetic crown to be used with a patient-specific abutment (e.g., which is a replica of the abutment analog). The prosthetic crown and the patient-specific abutment are then ready for placement on the implant 111 (FIG. 10) in the patient's mouth as a patient-specific prosthesis.

In a second alternative, no physical model of the patient's mouth is required. Rather, the modified virtual three-dimensional model 200A is used to design the prosthetic crown. The prosthetic crown (after it has been manufactured from the design) and the patient specific abutment are then ready for final placement on the implant 111 (FIG. 10) in the patient's mouth. In all of these options, it should be understood that a monolithic prosthetic device, which combines the patient-specific abutment and the prosthetic crown into a unitary piece, can also be the end-product from system using the modified virtual three-dimensional model 200A.

When the modified virtual three-dimensional model 200B including the virtual link abutment 620 is used (FIG. 18), the dental design software (or a user thereof) again accesses the publicly available library 355 with information about the virtual link abutment 620. Because the virtual link abutment 620 is a standard abutment with a known physical design, a patient-specific prosthesis (e.g., a patient-specific abutment and/or a patient-specific crown) to be mated to the virtual link abutment 620 can be designed through the dental design software. Accordingly, the patient-specific prosthesis and a physical link abutment (ceramic or titanium link abutment, which is not shown) are then ready for final placement on the implant 111 (FIG. 10) in the patient's mouth.

In a further alternative implementation, the dental design software permits a physical model of the patient's mouth to be designed and manufactured having a link-abutment analog therein. The link-abutment analog can be an integral structure with the rest of the model (e.g., a rapid-prototype model including a portion of a link-abutment therein made of the same material as the rest of the rapid-prototype model) or the link-abutment analog can be a separate and distinct component that is attached to or otherwise mated with a receptacle in the physical model such that the link-abutment analog is positioned with a location and orientation that corresponds with the implant in the mouth of the patient. The physical model of the patient's mouth that includes the link-abutment analog is then sent to a dental laboratory, which then performs standard wax up techniques on the physical model to develop a prosthetic crown that is to be used with the link abutment. The link abutment and the lab-developed prosthetic crown are then ready for placement on the implant 111 within the patient's mouth.

Figure 20:
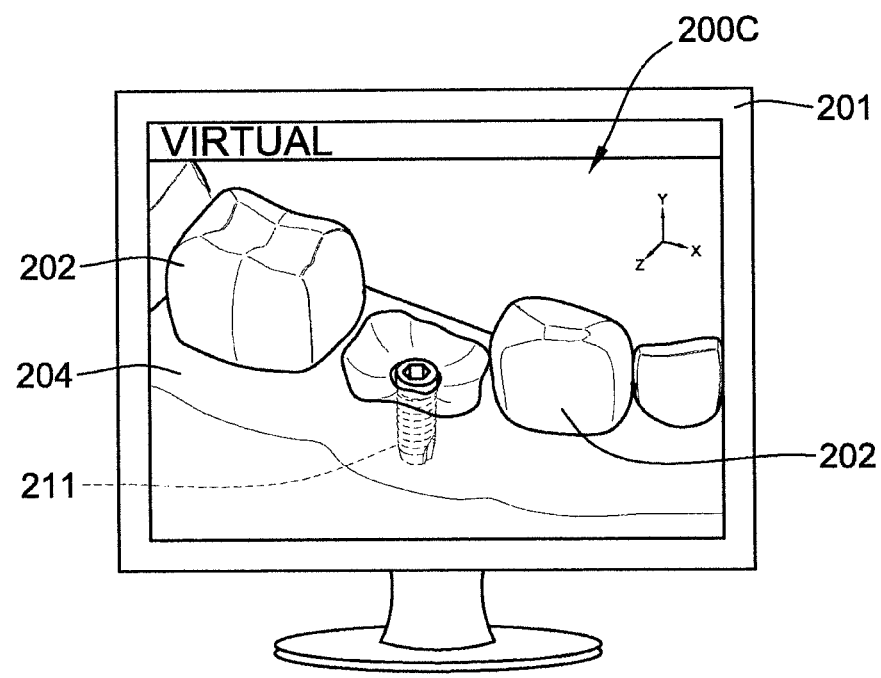
FIG. 20 illustrates a perspective view of a portion of a modified virtual three-dimensional model of the mouth of the patient where the virtual healing abutment of FIG. 12 has been removed and a virtual gingival aperture leading to a virtual implant is shown.

Referring generally to FIGS. 20, 21A, and 21B, where like reference numbers are used for like elements previous discussed, while the above disclosure discusses a modified virtual three-dimensional model 200A including a proxy abutment 220 (FIGS. 13 and 14), in lieu of using the modified virtual three-dimensional model 200A, an alternative modified virtual three-dimensional model 200D (FIGS. 21A and 21B) including a narrow virtual proxy abutment 820 can be used to design patient-specific components. The modified virtual three-dimensional model 200D (FIGS. 21A and 21B) is similar to the modified virtual three-dimensional model 200A (FIGS. 13 and 14) in many respects; however, instead of including the virtual proxy abutment 220, the modified virtual three-dimensional model 200D includes a narrow virtual proxy abutment 820 and a virtual gingival aperture 895.

As discussed above, using the identified orientation and size of the actual healing abutment 120 (e.g., determined using the code provided by the informational markers 126 on the healing abutment 120), the virtual three-dimensional model 200 (FIG. 12) can be modified to remove a portion thereof, thereby virtually exposing an underlying virtual implant 211 (FIG. 20) having an orientation (e.g., relative rotational position in space) and location (e.g., relative x-y-z position in space) corresponding to the orientation and location of the actual implant 111 in the mouth 100 of the patient 101. Additionally, the removal of the portion of the virtual three-dimensional model 200 (FIG. 12) can virtually expose the virtual gingival aperture 895 (best shown in FIG. 20) leading to the virtual implant 211, thereby creating a modified virtual three-dimensional model 200C. Again, by "virtually exposing," it is meant that the process of virtually removing the virtual healing abutment 210 can include virtually adding the virtual implant 211 or an upper portion thereof (e.g., a coordinate system for a virtual table) and the virtual gingival aperture 895 into the virtual three-dimensional model 200 because the information (e.g., exterior contours, location and orientation of non-rotational feature, etc.) about the virtual healing abutment 210 is known. The process for virtually exposing the virtual implant 211 and/or the virtual gingival aperture 895 is the same as, or similar to, the process described above in reference to FIGS. 12-14 for virtually exposing the virtual implant 211.

The modified virtual three-dimensional model 200C illustrates an intermediate step in the process of creating a virtual model (e.g., modified virtual three-dimensional model 200D shown in FIGS. 21A and 21B) including one of the virtual proxy abutments of the present disclosure (e.g., virtual proxy abutment 220, narrow virtual proxy abutment 820, floating virtual proxy abutment 920) for use in designing and fabricating patient-specific components (e.g., permanent and/or temporary patient-specific abutment, permanent and/or temporary patient-specific crown, etc.). While the modified virtual three-dimensional model 200C visually includes the virtual implant 211, the virtual implant 211 does not need to be included in the modified virtual three-dimensional model 200C. Rather, all that is needed for the inclusion of a virtual proxy abutment in the proper location (e.g., location and orientation corresponding to the virtual healing abutment 210) is a planar location along the Y-axis of the virtual table 219 (i.e., the upper surface) of the virtual implant 211 and the rotational location about the Y-axis of the non-rotational feature 218 (e.g., the hexagonal socket) of the virtual implant 211, both of which correspond with the location and orientation of the virtual healing abutment 210 removed from the virtual three-dimensional model 200 as described above.

After the virtual healing abutment 210 (FIG. 12) is removed and the virtual implant 211 and the virtual gingival aperture 895 are exposed, the narrow virtual proxy abutment 820 is imported into the modified virtual three-dimensional model 200C, thereby creating the modified virtual three-dimensional model 200D (FIGS. 21A and 21B). The narrow virtual proxy abutment 820 (FIGS. 21A and 21B) includes a relatively narrow shaft 820a attached to a spherical-like head 820b. The dimensions of the relatively narrow shaft 820a are selected such that the narrow virtual proxy abutment 820 does not visually obscure the virtual gingival aperture 895 when viewing the modified virtual three-dimensional model 200D, for example, using the computer 201. The narrow virtual proxy abutment 820 is positioned within the modified virtual three-dimensional model 200D such that a bottom planar surface 820a' of the shaft 820a is coplanar with the virtual table 219 (e.g., seating or upper surface) of the virtual implant 211 (which corresponds with the seating or upper surface of the implant 111 in the mouth of the patient), which is best shown in FIG. 21B. The bottom planar surface 820a' is so positioned whether the virtual implant 211 is included in the modified virtual three-dimensional model 200D or not. Further, the narrow virtual proxy abutment 820 is positioned within the modified virtual three-dimensional model 200D such that the narrow virtual proxy abutment 820 is contiguous with the surrounding features (e.g., the virtual implant 211, the virtual gingival aperture 895). By contiguous it is meant that the narrow shaft 820a is virtually touching the surrounding feature(s) in the modified virtual three-dimensional model 200D. In the implementation where the virtual implant 211 is not included in the modified virtual three-dimensional model 200D, the bottom planar surface 820a' is contiguous with the virtual gingival aperture 895. Such a contiguous narrow virtual proxy abutment 820 may be necessary in some design software packages that work from an abutment level model. For example, most design software packages only accept (1) a contiguous point cloud, (2) a contiguous surface mesh, (3) a contiguous surface model, or (4) a contiguous solid model, all of which are contiguous like the modified virtual three-dimensional model 200D.

It is noted that in the implementations including the virtual implant 211 in the modified virtual three-dimensional model 200D, the narrow virtual proxy abutment 820 is essentially included in the modified virtual three-dimensional model 200D because some design software packages may not be able to work directly from an implant coordinate position. Rather, some known design software packages are configured to start with an abutment level model such as the narrow virtual proxy abutment 820, where the abutment is first identified and then the implant is located relative to the identified abutment. The design software packages are used by labs to design and develop patient-specific components that are connected to the implant in the mouth of the patient. For example, a design software package is used to design a patient-specific abutment having a lower region that couples with the implant and has a size that matches the gingival contours in the patient's mouth. For another example, a design software package is used to design a patient-specific crown or restoration that is coupled to the implant in the patient's mouth via the patient-specific abutment. Examples of such dental design software packages are available from companies such as 3Shape A/S, Exocad® GmbH, E4D Technologies, and Sirona Dental Systems GmbH.

The spherical-like head 820b includes virtual proxy informational markers 826, which (like the virtual proxy informational markers 226) define a code corresponding with a proxy code, e.g., a proxy code of 1. The proxy code defined by the virtual proxy information markers 826 corresponds with the code on the virtual healing abutment 210 in the same, or similar, fashion that the virtual proxy informational markers 226 (FIG. 14) corresponds with the code on the virtual healing abutment 210. The main difference between the code on the narrow virtual proxy abutment 820 and the code on the virtual proxy abutment 220 is the form in how the code is illustrated and/or interpreted. For example, the virtual proxy informational markers 226 are depicted as a series of notches where the virtual proxy informational markers 826 are depicted as a triangle, a dot, and a dash. Regardless of the difference in appearance of the virtual proxy informational markers 226 and 826, the virtual proxy informational markers 826 provide a proxy code that can be interpreted to provide information regarding (1) the narrow virtual proxy abutment 820 itself (e.g., location of the narrow virtual proxy abutment 820 relative to the virtual implant, orientation of the narrow virtual proxy abutment 820 relative to the virtual implant, size of the narrow virtual proxy abutment 820, etc.), the virtual healing abutment 210, the actual healing abutment 120, the virtual implant 211, the actual implant 111, etc. As such, a dental laboratory having or viewing the modified virtual three-dimensional model 200D (FIGS. 21A and 21B) including the narrow virtual proxy abutment 820 can read the proxy code of 1 and reference a publicly available proxy abutment library 355 (FIG. 15) to identify the narrow virtual proxy abutment 820 (e.g., to determine the size and orientation of the narrow virtual proxy abutment 820). Once so identified, the location and orientation of the virtual implant 211 in the modified virtual three-dimensional model 200D can be determined and then used along with the virtual gingival aperture 895 to design and fabricate patient-specific components to be attached to the implant 111 in the same, or similar, fashion as described above.

Including the virtual gingival aperture 895 in the modified virtual three-dimensional model 200D can simplify the designing process for the lab receiving the modified virtual three-dimensional model 200D. Specifically, by including the virtual gingival aperture 895, the lab design software does not need to infer the virtual gingival aperture 895 from the virtual proxy abutment shape (e.g., exterior subgingival contours) when designing the patient-specific components as the virtual gingival aperture 895 is already included in the model. Further, including the virtual gingival aperture 895 in the modified virtual three-dimensional model 200D can be used to enable built-in functions of the lab design software, such as, for example, snap to gingiva, etc. Specifically, such a "snap to gingiva" function can be used when designing a patient-specific abutment to be attached to the implant in the mouth of the patient, where enabling or activating such a function causes the software to design the lower portion of the patient-specific abutment to have the same or corresponding contours as the virtual gingival aperture 895, thereby "snapping" the gingival contours in the modified virtual three-dimensional model 200D to the patient-specific abutment (not shown) being designed.

As shown in FIGS. 21A and 21B, the central axis of the narrow virtual proxy abutment 820 is positioned along the central axis of the virtual implant 211 and the top of the spherical-like head 820b is positioned a distance, $d_y$, above the virtual table 219 of the virtual implant 211. However, the narrow virtual proxy abutment 820 can have any orientation and/or be positioned anywhere in the modified virtual three-dimensional model 200D so long as the narrow virtual proxy abutment 820 (e.g., the spherical-like head 820b portion of the narrow virtual proxy abutment 820) has a specific X-Y-Z location—relative to an origin located at, for example, the virtual table 219 and the central axis of the virtual implant—that is determinable with reference to the library including the proxy code on the narrow virtual proxy abutment 820. Additionally, in some implementations, the distance, $d_y$, is a standard, publicly-known distance for all narrow virtual proxy abutments. In some alternative implementations, the distance, $d_y$, is provided by the proxy code on the narrow virtual proxy abutment 820.

As discussed above, the virtual proxy informational markers 826 provide a proxy code that can be interpreted to provide a variety of information (e.g., relative location, relative orientation, size, etc.) regarding the narrow virtual proxy abutment 820 itself, the virtual healing abutment 210, the actual healing abutment 120, the virtual implant 211, the actual implant 111, etc. In such implementations, a multitude of proxy codes are needed to identify the various implant types and connection sizes, etc. in the same manner as discussed above. For example, in an implementation including two different potential implant connections (e.g., internally connected implants, externally connected implants) and four different potential implant diameters (e.g., 3.4 mm, 4.1 mm, 5.0 mm, 6.0 mm), a library of eight different virtual proxy abutments having eight different proxy codes would be needed to provide enough information to the lab to design and fabricate the patient-specific components. Of course, such an implementation can include more than one proxy code for each implant connection and/or implant diameter as discussed above and/or can use the above described rolling code system to make it more difficult for unscrupulous competitive entities to identify and copy the codes for the healing abutments and/or the virtual proxy abutments.

Alternatively to having such a library with multiple proxy codes and virtual proxy abutments, the present disclosure can use a library with a single proxy code and a single proxy abutment (e.g., narrow virtual proxy abutment 820 or floating virtual proxy abutment 920). In such alternative implementations, the narrow virtual proxy abutment 820 provides a location and orientation of the virtual implant 211, but not the relevant connection and size (e.g., diameter) information of the virtual implant 211 nor the relevant gingival contour information of the healing abutment 120, which is provided by the virtual gingival aperture 895. Rather, such connection and size (e.g., diameter) information of the virtual implant 211 can be included in the modified virtual three-dimensional model 200D in a different manner, such as, for example, this information can be floating in a window 896 within the modified virtual three-dimensional model 200D (e.g., next to the spherical-like head 820b) as shown in FIG. 21A. Specifically, the window 896 includes information (e.g., alphanumeric information or data, pictorial information, etc.) indicating that the virtual implant 211 is a socket type connection (e.g., female non-rotational connection) and a table diameter of 3.4 mm. The floating information can automatically and/or manually be entered into the design software for use in connection with the virtual gingival aperture 895 and the proxy code to identify the proxy abutment and determine the location, orientation, connection, and size of the virtual implant, and then design and fabricate the patient-specific components therefrom. While the window 896 is shown in FIGS. 21A and 22A as indicating the implant connection and table diameter, the window 896 can include any information about the implant (e.g., manufacturer of the implant, length of the implant, thread pitch, diameter of the internal bore of the implant, tapered angle of the implant, etc.). While the window 896 is shown in FIGS. 21A and 22A as floating, the information contained in the window 896 can be provided in a variety of alternative manners, such as, for example, the information can be directly printed (i.e., virtually) or positioned on a surface of the narrow virtual proxy abutment 820 and/or elsewhere in the modified virtual three-dimensional model 200D.

As described in connection with FIGS. 21A and 21B, the narrow virtual proxy abutment 820 is contiguous with the surrounding features of the modified virtual three-dimensional model 200D because in some implementations, design software packages used by labs require a contiguous abutment level model. However, in some alternative implementations, such a contiguous virtual proxy abutment is not required. Now referring to FIGS. 22A and 22B, where like reference numbers are used for like elements previous discussed, a modified virtual three-dimensional model 200E includes a non-contiguous (e.g., virtually detached or virtually not touching) floating virtual proxy abutment 920. The modified virtual three-dimensional model 200E is the same as the modified virtual three-dimensional model 200D except that the narrow virtual proxy abutment 820 is replaced with the floating virtual proxy abutment 920. The floating virtual proxy abutment 920 is the same as the narrow virtual proxy abutment 820 except that the floating virtual proxy abutment 920 does not include the narrow shaft 820a of the narrow virtual proxy abutment 820. Specifically, the floating virtual proxy abutment 920 is same as the spherical-like head 820b of the narrow virtual proxy abutment 820. Other than the lack of the shaft 820a, the floating virtual proxy abutment 920 functions in substantially the same manner as the narrow virtual proxy abutment 820.

The floating virtual proxy abutment 920 is considered an "abutment" even though it does not "abut" the virtual implant 211 or the virtual gingival aperture 895 because the floating virtual proxy abutment 920 has a specific X-Y-Z location that is relative to the virtual implant 211 (e.g., the virtual table) and/or the virtual gingival aperture 895. The specific X-Y-Z location of the floating virtual proxy abutment 920 can be publicly known and the same for every floating virtual proxy abutment (e.g., always along the central axis of the virtual implant 211 and always with a distance $d_y$ of 10 mm) or different for every floating virtual proxy abutment. In the implementations where the specific X-Y-Z location of each floating virtual proxy abutment 920 is different, the specific X-Y-Z location is determinable with reference to a library (not shown) listing the X-Y-Z location next to the virtual proxy code formed by the virtual proxy informational markers 926 on the floating virtual proxy abutment 920.

In addition to using a rolling code system described above, the X-Y-Z location for the various floating virtual proxy abutments can be changed in a rolling fashion to further make it difficult for unscrupulous competitive entities to identify and copy the codes for the healing abutments and/or the virtual proxy abutments. For example, during a first period of time as shown in FIGS. 22A and 22B, the floating virtual healing abutment 920 is associated with a first X-Y-Z location relative to the virtual implant (e.g., along the central axis of the virtual implant 211 and with a distance $d_y$ of 10 mm). The manufacturer and/or the entity creating the modified virtual three-dimensional models (e.g., models 200A, 200B, 200D, 200E) can then switch the X-Y-Z location for the floating virtual healing abutment 920 for a second period of time where the floating virtual healing abutment 920 is associated with a second X-Y-Z position (not shown) that is different than the first X-Y-Z position (e.g., along a second axis that is parallel with and offset by 5 mm from the central axis of the virtual implant 211 and with a distance $d_y$ of 20 mm).

While the floating virtual proxy abutment 920 is shown and described as having a specific X-Y-Z location relative to the rest of the modified virtual three-dimensional model 200E, it should be understood that the floating virtual proxy abutment 920 can be positioned in any X-Y-Z location so long as the floating virtual proxy abutment 920 does not obscure the virtual gingival aperture 895 to be used in designing the patient-specific components. One of the important points about the narrow virtual healing abutment 820 and the floating virtual proxy abutment 920 is that they both do not obscure the virtual gingival aperture 895 in the modified virtual three-dimensional models 200D and 200E, respectively.

The narrow virtual proxy abutment 820 is described and shown as including the spherical-like head 820b and the non-contiguous floating virtual proxy abutment 920 is described and shown as being the same as the spherical-like head 820b of the narrow virtual proxy abutment 820, both of which are shown as being spherical-like (e.g., having a generally spherical shape); however, the spherical-like head 820b and the floating virtual proxy abutment 920 can have a variety of shapes and/or sizes. For example, the spherical-like head 820b and the floating virtual proxy abutment 920 can have an elliptical shape, a square shape, a rectangular shape, a polygonal shape, a triangular shape, or any combination thereof.

While FIGS. 21B and 22B are shown as being cross-sectional views of FIGS. 21A and 22A, respectively, it is noted that in some implementations, the modified virtual three-dimensional models 200D and 200E depict (1) components representative of actual physical components (e.g., teeth, gingiva, etc.) and (2) some purely virtual components without a real corresponding component (e.g., virtual proxy abutment), where all of the virtually depicted components in the models 200D and 200E do not have a thickness (e.g., are not solid components), but rather are just zero-thickness point clouds or a mesh of surface data (e.g., similar to how a balloon is not solid as distinguished from an ice cube that is solid). As such, the cross-sectional views of the models 200D and 200E depicted in FIGS. 21B and 22B do not include cross hatching.

In summary, the present disclosure can be used to design and manufacture patient-specific prostheses including customized patient-specific crowns and/or patient-specific abutments. The customized crown can be designed directly from the modified virtual three-dimensional models 200A, 200B, 200D, and 200E and subsequently manufactured. Or, the crown can be manufactured through more common laboratory techniques if a physical model of the patient's mouth is made from the modified virtual three-dimensional models 200A, 200B, 200D, and 200E after the details of the patient-specific abutment or the link abutment are determined. Or, a combination of the two techniques can be used where a portion of the patient specific prosthesis is designed directly from the modified virtual three-dimensional models 200A, 200B, 200D, and 200E and subsequently manufactured and then mated with a physical model of the patient's mouth to finalize the fabrication of the patient-specific prosthesis (e.g., add a final porcelain coating).

While the present disclosure has been described with reference to one or more particular implementations, those skilled in the art will recognize that many changes may be made thereto without departing from the spirit and scope of the present disclosure. Each of these implementations and obvious variations thereof is contemplated as falling within the spirit and scope of the present disclosure, which is set forth in the claims that follow.

What is claimed is:

1. A method for developing a patient-specific prosthesis to be coupled to an implant installed in a mouth of a patient, the method comprising:

scanning a scanning member that is attached to the implant to obtain scan data, the scanning member having a top surface with a first code thereon, the first code being indicative of a first size of the scanning member and an orientation of a non-rotational fitting of the scanning member;

from the scan data, creating a virtual three-dimensional model of the mouth, the virtual three-dimensional model including a virtual scanning member with a first virtual code thereon, the first virtual code corresponding to the first code on the scanning member attached to the implant in the mouth of the patient;

obtaining, from the virtual three-dimensional model, the first virtual code associated with the virtual scanning member;

based on a scanning-member library, determining the first size of the scanning member from the first virtual code, wherein the scanning-member library correlates the first virtual code indicative of the first size that corresponds to the first code, wherein the scanning-member library includes a second virtual code different from the first virtual code, the second virtual code indicative of a second size that corresponds to a second code different from the first code, wherein the second size is the same as the first size;

based on the first virtual code, determining the orientation of the non-rotational fitting of the scanning member;

replacing the virtual scanning member in the virtual three-dimensional model with a virtual proxy abutment to create a modified virtual three-dimensional model, the virtual proxy abutment having known characteristics for determining a location and an orientation for the patient-specific prosthesis to be attached to the implant;

designing, by use of the virtual proxy abutment, the patient-specific prosthesis to be coupled to the implant in the mouth of the patient; and fabricating the patient-specific prosthesis to be coupled to the implant in the mouth of the patient.

2. The method of claim 1, wherein the designing includes accessing a proxy-abutment database that relates a virtual proxy code to the known characteristics.

3. The method of claim 2, wherein the virtual proxy code is located at an upper surface of the virtual proxy abutment.

4. The method of claim 1, wherein the virtual proxy abutment is used for multiple sizes of scanning members.

5. The method of claim 4, wherein the multiple sizes corresponds to scanning members having different heights.

6. The method of claim 1, wherein the virtual proxy abutment has a virtual proxy code that is indicative of that particular virtual proxy abutment.

7. The method of claim 1, wherein the virtual proxy abutment is a different size than the scanning member.

8. The method of claim 1, wherein the scanning member is a healing abutment.

9. The method of claim 1, wherein the scanning member is a component of a temporary prosthesis.

10. The method of claim 1, wherein the replacing further comprises replacing the virtual scanning member in the virtual three-dimensional model with a virtual gingival aperture in addition to the virtual proxy abutment to create the modified virtual three-dimensional model, the virtual gingival aperture corresponding to a size of at least a portion of the scanning member.

11. The method of claim 10, wherein the designing further comprises designing by use of the virtual gingival aperture in addition to the use of the virtual proxy abutment.

12. The method of claim 10, wherein the at least a portion of the scanning member is a subgingival portion of the scanning member.

13. The method of claim 10, wherein the virtual gingival aperture includes virtual gingival contours that correspond with outer contours of the scanning member.

14. The method of claim 10, wherein the virtual proxy abutment is a narrow virtual proxy abutment including a shaft and a head, the shaft being contiguous with the virtual gingival aperture in the modified virtual three-dimensional model.

15. The method of claim 14, wherein the narrow virtual proxy abutment is sized and positioned within the modified virtual three-dimensional model such that the virtual gingival aperture remains visible.

16. The method of claim 10, wherein the virtual proxy abutment is a floating virtual proxy abutment, the floating virtual proxy abutment being virtually detached from the rest of the depicted elements in the modified virtual three-dimensional model.

17. The method of claim 16, wherein the floating virtual proxy abutment is sized and positioned within the modified virtual three-dimensional model such that the virtual gingival aperture remains visible.

18. The method of claim 10, wherein the replacing further includes replacing the virtual scanning member with a window including information associated with the implant installed in the mouth, the window being virtually detached from the rest of the depicted elements in the modified virtual three-dimensional model.

19. The method of claim 18, wherein the information included in the window is alphanumeric data.

20. The method of claim 18, wherein the information includes an implant connection type, an implant table diameter, or both.

* * * * *